(12) United States Patent
Watanabe et al.

(10) Patent No.: US 7,553,640 B2
(45) Date of Patent: Jun. 30, 2009

(54) SAPONIN-DECOMPOSING ENZYME, GENE THEREOF AND LARGE-SCALE PRODUCTION SYSTEM FOR PRODUCING SOYASAPOGENOL B

(75) Inventors: Manabu Watanabe, Odawara (JP); Naoki Mido, Odawara (JP); Takayoshi Tamura, Odawara (JP); Naomi Sumida, Odawara (JP); Takashi Yaguchi, Odawara (JP)

(73) Assignee: Meiji Seika Kaisha, Ltd., Tokyo (JP)

( * ) Notice: Subject to any disclaimer, the term of this patent is extended or adjusted under 35 U.S.C. 154(b) by 0 days.

(21) Appl. No.: 12/010,055

(22) Filed: Jan. 18, 2008

(65) Prior Publication Data

US 2008/0187972 A1 Aug. 7, 2008

Related U.S. Application Data

(62) Division of application No. 11/504,646, filed on Aug. 16, 2006, now Pat. No. 7,335,498, which is a division of application No. 11/320,412, filed on Dec. 29, 2005, now Pat. No. 7,144,718, which is a division of application No. 10/479,787, filed as application No. PCT/JP02/005615 on Jun. 6, 2002, now Pat. No. 7,022,508.

(30) Foreign Application Priority Data

Jun. 6, 2001 (JP) .............................. 2001-171604

(51) Int. Cl.
*C07H 21/04* (2006.01)
*C12N 9/24* (2006.01)
*C12Q 1/68* (2006.01)

(52) U.S. Cl. ................. 435/69.1; 435/200; 435/254.11; 435/252.1

(58) Field of Classification Search ........................ None
See application file for complete search history.

(56) References Cited

U.S. PATENT DOCUMENTS 6,277,596 B1 8/2001 Watanabe et al.
2004/0029214 A1 2/2004 Yaguchi et al.

FOREIGN PATENT DOCUMENTS

| JP | 4-267876 | 9/1992 |
| JP | 10-234396 | 9/1998 |
| WO | 95/30009 | 11/1995 |
| WO | 98/11239 | 3/1998 |
| WO | 01/81612 | 11/2001 |

OTHER PUBLICATIONS

S. Kudou et al., "Purification and some properties of soybean saponin hydrolase from *Aspergillus oryzae* KO-2", Agric. Biol. Chem., Jan. 1991, vol. 55, No. 1, pp. 31-36.
S. Kudou et al., "Screening for microorganisms producing soybean saponin hydrolase", Agric. Biol. Chem., 1990, vol. 54, No. 11, pp. 3035-3037.
Y. Sasaki et al., "Substrate specificity of glycyrrhizinic acid hydrolase", Agric. Biol. Chem., 1998, vol. 52, No. 1, pp. 207-210.
Accession No. 1979: 143769, E.D. Biosis Perepelista et al., "Use of hydrolytic enzymes of the fungus *Aspergillus niger* BKMT-33 to increase diosgenin yield from *Tribulus terrestris*", Prikl Biokhim Mikrobiol, 1978, vol. 14, No. 2, pp. 309-312.
Watanabe et al., "A Novel Saponin Hydrolase from *Neocosmospora vasinfecto* var. *vasinfecta*," Applied and Environmental Microbiology, vol. 70, No. 2, pp. 865-872, 2004.
Japanese Patent Office Office Action dated Mar. 14, 2008 in Japanese Application No. 2003-503803.

*Primary Examiner*—Jon P Weber
*Assistant Examiner*—Kagnew H Gebreyesus
(74) *Attorney, Agent, or Firm*—Wenderoth, Lind & Ponack, L.L.P.

(57) ABSTRACT

The present invention provides a protein having saponin-decomposing activity, more specifically a protein which can decompose a glycoside having soyasapogenol B as an aglycone to produce soyasapogenol B, a polynucleotide encoding such a protein, and a method of producing soyasapogenol B on a large scale using the same. A protein according to the present invention are concerned with (a), (b) or (c), namely (a) a protein comprising an amino acid sequence selected from the group consisting of the amino acid sequences shown in SEQ ID NOs: 2, 4, and 6; (b) a protein that has at least 50% homology to the protein comprising the amino acid sequence of the sequence described in (a) and having saponin-decomposing activity; or (c) a protein comprising a modified amino acid sequence of the sequence described in (a) that has one or more amino acid residues deleted, substituted, inserted, or added and having saponin-decomposing activity.

3 Claims, 10 Drawing Sheets

```
SDA_mat.ptn    1:QQILK---P-PVPEPIVVTELPLPPVADSKEGS-CTPEVSPHRTGCLLKSSQ--IQSGNF   53
SDE_mat.ptn    1:STT----PAPPQPEPIEVVELPLPPVAPSNSTGACTASINPHRTGCIAQVSDSFQA-GDF   55
SDN_mat.ptn    1:ASPPASVPNPPSPEPITLKQLPLPPISPSDDVGACTKQINSRGTGCLANGVFETFQSGDF   60
                 . .* ****. . *****...*  ..**  .....***..  .   ..*.*
SDA_mat.ptn   54:LPDNNHVLVSLNFSGAPAAPDPASIYNGTHLTLIKADGTNFPSGDPWKCITCGVPEENKV  113
SDE_mat.ptn   56:TPDGNHVVITVEFVGAPAAPDPASIYSGEHIILVKADGTTFTNGDAWKCLSCGVPSKNAL  115
SDN_mat.ptn   61:LPDGKHVIAMVNFTGAPAAPAAGSIYSGPQVIIVKTDGKTFPNGDPWKCITCGVPEKNAV  120
                 .**..**   ..* *******...***.*  .....*..**..*.. **.***..****..*..
SDA_mat.ptn  114:GSTELSPYPQAFLDGKRALIGTNIVOCGSALLSSSDCTPDKVHIYPIRWNVKADGSGSGG  173
SDE_mat.ptn  116:SLDPQRDYPHVARNSRQALWGHNILDCSGIPLVSDECTPNKTHIYP1YWPTGTNSSGS--  173
SDN_mat.ptn  121:GISVKYDYPQAFKDGKRLLIGHNILDCGTNQLTSESCKPDNTHIYPIRWNVAADGSGPSG  180
                 .   .**...  .....*.*.**.**.   * *  *.*...*****.*. ...**. .
SDA_mat.ptn  174:NIRELRLHPDNVHLGFNSFTFSNGQLGQFGYFSRLQFNPAPKTGEPRSARYDLVNYTRLY  233
SDE_mat.ptn  174:-TREMRLHPDDTHMGWSSFTSG----GQFAYFGRLQFRQNPTDGTLRVPRYDLVDVNLLV  228
SDN_mat.ptn  181:EIRELRLHPDNVHLEFSSFTFASGSIGQYAYFSRLVFNPSPKTGTPLAPRYDLEKVTILH  240
                 .**.*****..*....***.  .  **..**.**.*..  *..*...  .****.*. *
SDA_mat.ptn  234:NPDSPQPJSAKGNELLFNRSAIAVGELRGFTGRCKEVTYIGNPVESCNIDVFAADLTTGK  293
SDE_mat.ptn  229:QPNGTAPIMAQGSELKIHNEAITVGELRGFSGAGDEILYIGSTREANNIDLFAVHITTGA  288
SDN_mat.ptn  241:NPEGVAPITAKGKVLSLNPQAISVGEARGFNGDGTELTYVGSNIESCNNDVFAVHLQTGV  300
                 .* ..** *.*.* . ** ***.*** * * .*.*.  *..*.*.**...**
SDA_mat.ptn  294:VRRITDHPEYVDPMDVSPDDKWQVILDTRGTGRQMFMAGMRGIPPIIDLIATTVASSTRN  353
SDE_mat.ptn  289:VRRLTSHPEYADPIAFSHDNQWFVTMDTRGSNRQMWMAGERYIPPLIDLVTVTAASSTRN  348
SDN_mat.ptn  301:VRRLTNHPEYPDPLAFSPDNKWMAVMDTRGSGRNMFIAGMRGIPPLVDIVGGILPASSRN  360
                 ***.* ****.**  ..*.*..*.  . ****..*.*..**.*.***..*.    ...*.**
SDA_mat.ptn  354:NGPRRFFRPWLLDHDGDRGDYYGQQINGDGDGSPGS--INDPNWNAGADPKWSHDGTRIA  411
SDE_mat.ptn  349:NGARRFFQPILIDRYGDRGDYFGQRVNYQGDGSNGS--VNDPNWNGRADPAFSPDGTRIV  406
SDN_mat.ptn  361:NGLRRFFQPYLLDFYGDRGDYYGQKINGDNNGVPGSGAINDPEWNGMADPRWSPDSRQLV  420
                 ** ****.* *.*  ,******.**  .*....*..** . ***.**. *** .*.*.....
SDA_mat.ptn  412:YFENLVVSPSCGGQNPLPC-PNSTEPGGRVTRLMLAHLTSREPLDLEPVAPVSDEVPWGV  470
SDE_mat.ptn  407:YWQALVIPPACGGANPLPCPVSTAQG-GRTYRVMLARLSDRKHTDPAPVFAAPDYISWAT  465
SDN_mat.ptn  421:FWQTHTVSPSCGGANPLPCYPSK-EQGGRNYRMYIATFTSRSPSPPAPVKEHSDTIPWGV  479
                 ... ,,,,*. ***. *****  ..   .  ** *  ...**   .* ..**..
SDA_mat.ptn  471:PYVPESALPDRP-FPAEGNYTLKGEVSGSASVSIIHDKTIPAAIKTIAVTYRNYSDDGLH  529
SDE_mat.ptn  466:PFPPGAGLPTSYTLPA-GNYTLYGKATGLANATLTRDPLFGSFKTVS-VNYTNFSDDGQH  523
SDN_mat.ptn  480:PYVPGSQVTPKPGL-AGGIYTLYGKASGEAKVNITWGEAPEIG--TVSVVYKDYSLDGKS  536
                 *..*.. ..    ...* * ***.*...* *. ...   .   *  *..*.**.
SDA_mat.ptn  530:VIAGSERFTNTVASMTINKV--DWFSDLTSTGQVTGSKKTSPGGFHLEIDAMTNIFMANG  587
SDE_mat.ptn  524:FINGYESVTLTLSASNPWLSHLDWVSDIVQTGAVNAVKETGSGGFHLTIDAQENIFEANG  583
SDN_mat.ptn  537:FLNGNESVTGSVERLTDYSF--DWYSDIRQTGAVKGTKKTSPGGFHANIDVMINDLTSTG  594
                 ...* *..* ..  .        ** **. .**.*  . *.*. ,****. **,.  *.. ...*
SDA_mat.ptn  588:TLTTTIDGKVWKQPANGT                                           605
SDE_mat.ptn  584:TLTTTVDGVTYHQPLNGA                                           601
SDN_mat.ptn  595:TLTTTLDGVEWRSPQSGT                                           612
                 ***** **. . .*. *.
```

FIG.10

SAPONIN-DECOMPOSING ENZYME, GENE THEREOF AND LARGE-SCALE PRODUCTION SYSTEM FOR PRODUCING SOYASAPOGENOL B

This application is a divisional of Ser. No. 11/504,646, filed Aug. 16, 2006 now U.S. Pat. No. 7,335,498, now allowed, which is a divisional of Ser. No. 11/320,412, filed Dec. 29, 2005, now U.S. Pat. No. 7,144,718, which is a divisional of Ser. No. 10/479,787, filed Dec. 5, 2003, now U.S. Pat. No. 7,022,508, which is a 371 U.S. national stage of International Application No. PCT/JP02/05615, filed Jun. 6, 2002. The above-referenced applications are hereby incorporated by reference.

BACKGROUND OF THE INVENTION

1. Field of the Invention

The present invention relates to a novel saponin-decomposing enzyme, a gene thereof, and a novel method for producing soyasapogenol B using them.

2. Background Art

Soyasapogenol B (12-oleanane-3,22,24-triol) is one of the aglycones of saponins contained in legumes and has been reported to have various physiological activities since early times. For example, platelet aggregation suppressing effect, anticomplementary activity, and preventive and therapeutic activity for nephritis, rheumatism, immune diseases such as systemic lupus erythematosus, autoimmune diseases or thrombosis have been reported (Chem. Pharm. Bull., 24, 121-129, 1976; Chem. Pharm. Bull., 30, 2294-2297, 1982; Kagaku to Seibutsu, 21, 224-232, 1983; Japanese Patent Application Laid-open No. 37749/1986). Further, growth-suppressing effect on cells derived from human colon cancer and human ovarian cancer has been reported (Japanese Patent Application Laid-open No. 37749/1986; Japanese Patent Application Laid-open No. 234396/1998).

Soyasapogenol B can be produced, for example, by chemically hydrolyzing sugar chains of saponins contained in soybean seeds as glycosides (soyasaponins I-V). However, this is not an effective production method because a considerable number of by-products may be produced depending on the conditions for acid hydrolysis. Further, soybean seeds are known also to contain saponins which have soyasapogenol A (soyasaponins A1-A6) or soyasapogenol E as an aglycone. Therefore, when soyasapogenol B is prepared from soybeans, the resulting preparation may easily contain soyasapogenol A and soyasapogenol E as impurities so that it is difficult to purify soyasapogenol B alone from such preparation. Further, since the saponin content of soybean seeds is generally as low as about 0.2% (Yakugaku Zasshi, 104, 162-168, 1984), there is a need for more efficient production.

As for methods of producing soyasapogenol B using microorganisms, a method with genus *Streptomyces* (Chem. Pharm. Bull. 32: 1287-1293, 1984) and a method with genus *Penicillium* (Japanese Patent Application Laid-open No. 234396/1998) is known. However, these methods of producing soyasapogenol B using microorganisms are poor in productivity and practicality.

Further, it has been reported that soyasapogenol B can be obtained as a by-product in a method in which an acid oligosaccharide having glucuronic acid as the reduced end is produced by hydrolyzing a glucuronide saponin using the enzyme (glucuronidase) produced by microorganisms that belong to genus *Aspergillus* or a culture containing this enzyme (Japanese Patent Publication No. 32714/1995). However, this method is primarily a method of producing acid oligosuccharides, and only a qualitative confirmation of soyasapogenol B is described in this report. Further, this report revealed the molecular weight of the enzyme having activity of interest but not the amino acid sequence thereof.

On the other hand, the search for microorganisms which efficiently produce soyasapogenol B by selectively hydrolyzing a glycoside having soyasapogenol B as an aglycone resulted in finding filamentous fungus strains that belong to genus *Neocosmospora* or genus *Eupenicillium*. It has been found that soyasapogenol B is produced and accumulated in a culture medium at a high concentration by culturing filamentous fungi, that belong to genus *Neocosmospora* or genus *Eupenicillium*, in a medium containing a saponin (a glycoside having soyasapogenol B as an aglycone) (see WO 01/81612).

Examples of such filamentous fungi include *Neocosmospora vasinfecta* var. *vasinfecta* PF1225 that belongs to genus *Neocosmospora* and *Eupenicillium brefeldianum* PF1226 that belongs to genus *Eupenicillium* (see WO 01/81612).

Soyasapogenol B of interest can be produced using such fungi as they are, depending on the amount of saponins added to the medium. However, the amount of saponins to be added to the medium is limited because of the surface-active property of saponins, which easily foam. Further, viscosity of the medium supplemented with saponins is expected to increase because of the surface-active property. Accordingly, in order to improve the yield in producing the target substance from the culture, the extraction process has to be repeated several times. Further, soybean extract, which is generally used as a natural resource to effectively supply saponins, usually contains components other than saponins, such as lipids, proteins and polysaccharides. Therefore, the possible amount of saponins to be added to a medium ultimately depends on the purity of the soybean extract, which does not necessarily assure efficient production.

There is a need to develop a method for the large scale production of soyasapogenol B by an enzyme reaction using a saponin-decomposing enzyme producing enzyme, in which soyasapogenol B is efficiently produced and a high yield is maintained independently of the saponin content in a soybean extract, contrary to conventional methods.

SUMMARY OF THE INVENTION

Recently, the present inventors succeeded in isolating and purifying a protein having saponin-decomposing activity from microorganisms having saponin-decomposing activity (occasionally called "saponin-decomposing enzyme" hereinafter) and in identifying a gene encoding this protein. Further, the present inventors were able to obtain a highly active saponin-decomposing enzyme by expressing the resulting gene in a heterologous host. Further, the present inventors were able to effectively produce soyasapogenol B by carrying out an enzyme reaction using the saponin-decomposing enzyme thus obtained. The present invention is based on these findings.

Accordingly, an objective of the present invention is to provide a protein having saponin-decomposing activity, more specifically a protein which can decompose a glycoside having soyasapogenol B as an aglycone to produce soyasapogenol B, a polynucleotide encoding such protein, and a method of producing soyasapogenol B on a large scale using the same.

A protein according to the present invention is selected from the group consisting of the followings:

(a) a protein comprising an amino acid sequence selected from the group consisting of the amino acid sequences shown in SEQ ID NOs: 2, 4, and 6;

(b) a protein that has at least 50% homology to the protein comprising the amino acid sequence of the sequence described in (a) and having saponin-decomposing activity; and (c) a protein comprising a modified amino acid sequence of the sequence described in (a) that has one or more amino acid residues deleted, substituted, inserted, or added and having saponin-decomposing activity.

A polynucleotide according to the present invention is selected from the group consisting of the followings:

(i) a polynucleotide consisting of a DNA sequence selected from the group consisting of the DNA sequences of SEQ ID NOs: 1, 3, and 5;

(ii) a polynucleotide that has at least 70% homology to the polynucleotide consisting of the DNA sequence of (i) and encodes a protein having saponin-decomposing activity;

(iii) a polynucleotide consisting of a modified DNA sequence of the sequence described in (i) that has one or more bases deleted, substituted, inserted, or added and encodes a protein having saponin-decomposing activity; and (iv) a polynucleotide that hybridizes with a polynucleotide comprising the DNA sequence described in (i) under stringent conditions and encodes a protein having saponin-decomposing activity.

A recombinant vector according to the present invention comprises a polynucleotide of the present invention.

Further, a host according to the present invention is a host transformed with the abovementioned recombinant vector.

A process for producing a protein of interest according to the present invention comprises culturing the abovementioned transformed host and collecting a protein having saponin-decomposing activity from the resulting culture.

According to the present invention, a highly active saponin-decomposing enzyme can be obtained. Further, by using this enzyme, soyasapogenol B can be obtained efficiently and on a large scale from saponin. According to this method, soyasapogenol B can be obtained independently of the saponin content of, for example, a soybean extract.

BRIEF DESCRIPTION OF THE DRAWINGS

FIG. 10 shows the results made by a comparison between SDN, SOA and SOE by searching their homology to each other—the sequence of the top line is SEQ ID NO: 4, the sequence of the middle line is SEQ ID NO: 6 and the sequence of the bottom line is SEQ ID NO: 2.

DETAILED DESCRIPTION OF THE INVENTION

Deposition of Microorganisms

Figure 1:
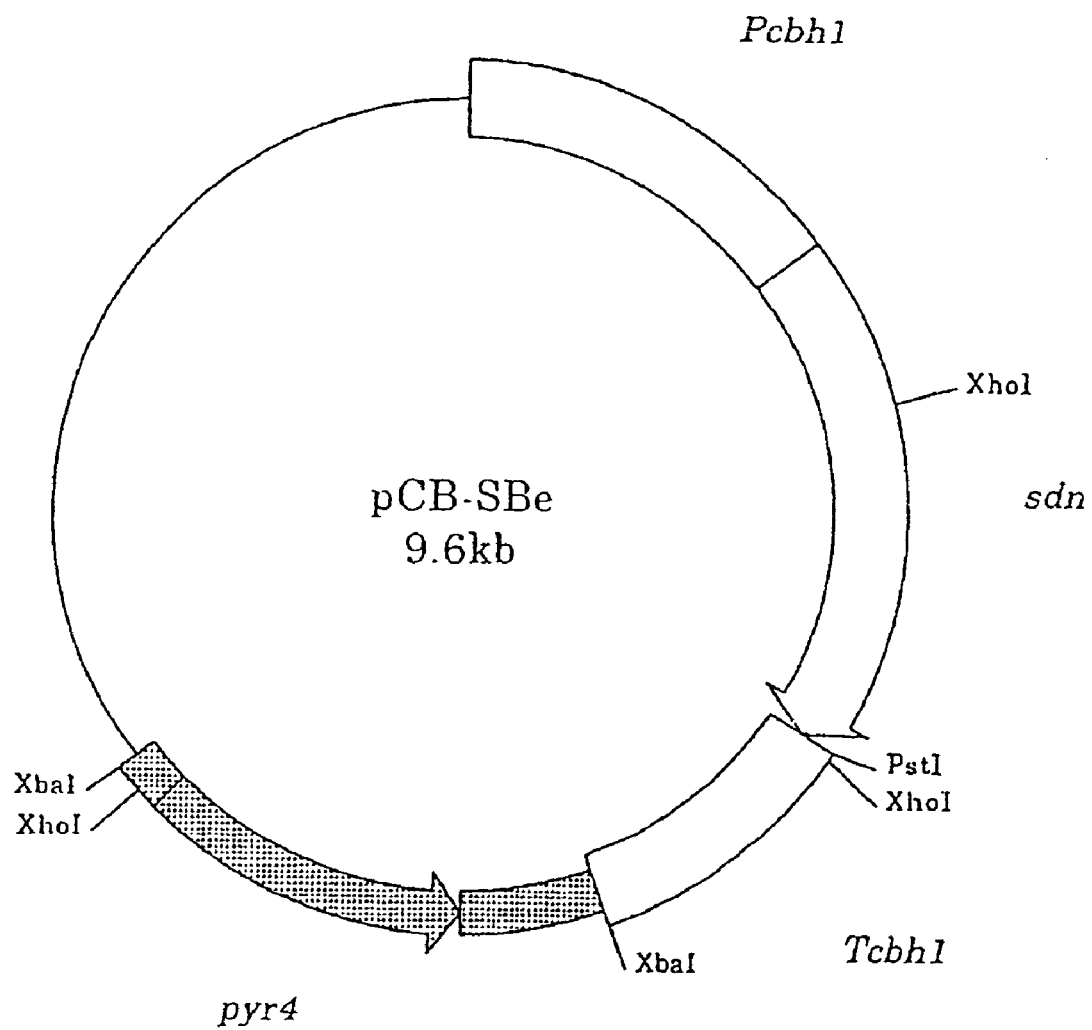
FIG. 1 shows the construction and restriction map for plasmid pCB-SBe.

The strain *Neocosmospora vasinfecta* var. *vasinfecta* PF1225 was deposited with the International Patent Organism Depositary, National Institute of Advanced Industrial Science and Technology, AIST Tsukuba Central 6, 1-1-1 Higashi, Tsukuba, Ibaraki, Japan 305-5466, dated Mar. 13, 2000 (original deposition date). The accession number is FERM BP-7475.

The strain *Eupenicillium brefeldianum* PF1226 was deposited with the International Patent Organism Depositary, National Institute of Advanced Industrial Science and Technology, AIST Tsukuba Central 6, 1-1-1 Higashi, Tsukuba, Ibaraki, Japan 305-5466, dated Mar. 13, 2000 (original deposition date). The accession number is FERM BP-7476.

The strain *Aspergillus* sp. PF1224 was deposited with the International Patent Organism Depositary, National Institute of Advanced Industrial Science and Technology, AIST Tsukuba Central 6, 1-1-1 Higashi, Tsukuba, Ibaraki, Japan 305-5466, dated May 24, 2001. The accession number is FERM BP-8004.

The strain *Trichoderma viride* MC300-1 was deposited with the International Patent Organism Depositary, National Institute of Advanced Industrial Science and Technology, AIST Tsukuba Central 6, 1-1-1 Higashi, Tsukuba, Ibaraki, Japan 305-5466, dated Sep. 9, 1996 (original deposition date). The accession number is FERM BP-6047.

Protein Having Saponin-Decomposing Activity

A saponin-decomposing enzyme isolated and purified from *Neocosmospora vasinfecta* var. *vasinfecta* PF1225 (FERM BP-7475) was revealed to be a novel enzyme system since it has no homology to any saponin-decomposing enzyme found to date and is different from glucuronidase derived from a microorganism belonging to genus *Aspergillus* (a glycoprotein having a molecular weight of about 158,000 consisting of subunits each having a molecular weight of 35,000 and 45,000 described in Japanese Patent Publication No. 32714/1995), which decomposes glucuronide saponin, in its subunit structure and molecular weight.

Further, the protein according to the present invention and glucuronidase previously disclosed in the Patent Publication were studied for their identity and homology. Since the strain belonging to genus *Aspergillus* described in said Patent Publication was not readily available, another strain belonging to genus *Aspergillus* was used. The strain used was *Aspergillus* sp. PF1224, which was identified to be a filamentous fungus, Deuteromycetes, belonging to genus *Aspergillus* according to the microbial properties shown below.

(1) Colony Features

Colonies grow well on a Czapek's yeast extract agar medium at 25° C. attaining a diameter of 80 mm in 7 days. The colonies are yellow to yellowish green, woolly and rich in conidia and sclerotia. The reverse side becomes pale brown. Colonies grow well on a malt extract agar medium at 25° C. attaining a diameter of 80 mm in 7 days.

The colonies are yellow to yellowish green, woolly and rich in conidia and sclerotia. The reverse side becomes ocherous. Colonies are slightly suppressed on either medium when cultured at 37° C.

(2) Morphological Features

Conidial heads are yellow to yellowish green and radiate to loose cylindrical. Conidiophores are rough and colorless and vesicles are rodlike to subglobose, bearing aspergilla on almost the entire surface. Monoseriate and biseriate aspergilla are mixed; they are generally biseriate. Metulae are 8-12×4-5 μm and phialides are 8-12×3-4 μm. Conidia are globose to subglobose, rough, and 4-6 μm in length.

The enzyme referred to as glucuronidase was confirmed using *Aspergillus* sp. PF1224, which revealed that the saponin-decomposing enzyme isolated and purified from *Aspergillus* sp. PF1224 by the present inventors has a molecular weight of 90 kDa, an optimum pH of 5 to 6, and an optimum temperature of 45° C. to 50° C. (see Reference Example). Furthermore, it was revealed that the saponin-decomposing enzyme isolated and purified from *Eupenicillium brefeldianum* PF1226 has a molecular weight of 90 kDa, an optimum pH of 5 to 6, and an optimum temperature of 40° C. to 45° C.

The protein of the present invention and the glucuronidase described in the abovementioned Patent Publication were compared for their molecular weight and subunit configuration since information such as an amino acid sequence of glucuronidase was not disclosed in this Patent Publication to compare homology of the amino acid sequence or the like. Results showed that the protein according to present invention is a protein different from the glucuronidase described in the Patent Publication.

As mentioned above, the present invention provides a protein selected from the group consisting of:

(a) a protein comprising an amino acid sequence selected from the group consisting of the amino acid sequences shown in SEQ ID NOs: 2, 4, and 6;

(b) a protein that has at least 50% homology to the protein comprising the amino acid sequence of the sequence described in (a) and having saponin-decomposing activity; and (c) a protein comprising a modified amino acid sequence of the sequence described in (a) that has one or more amino acid residues deleted, substituted, inserted, or added and having saponin-decomposing activity.

Namely, a protein according to the present invention comprises an amino acid sequence which is identical or substantially identical to the amino acid sequence shown in SEQ ID NO: 2, 4, or 6.

An amino acid sequence that is substantially identical to the amino acid sequence shown in SEQ ID NO: 2, 4, or 6 herein means an amino acid that is typically more than 50%, preferably more than 70%, more preferably more than 80%, further preferably more than 90%, furthermore preferably more than 95%, or most preferably more than 98% homologous to any one of the amino acid sequences shown in these SEQ ID NOs.

Further, these figures for homology shown in the present specification can be any figures calculated using a homology search program known to the skilled in the art. For example, figures can be readily calculated using default parameters in FASTA, BLAST, or the like.

For example, when the figures for homology has been calculated using default parameters in the homology search program Genetyx (manufactured by Genetyx Co.), the figure for homology between SDN and SDA is 51%, that between SDA and SDE is 52%, and that between SDE and SDN is 51%.

Further, a protein comprising an amino acid sequence that is substantially identical to the amino acid sequence shown in SEQ ID NO: 2, 4, or 6 means a protein comprising a modified amino acid sequence that has one or more amino acid residues deleted, substituted, inserted, or added and having saponin-decomposing activity.

The number of amino acid residues that can be deleted, substituted, inserted, or added is preferably 1 to 50, more preferably 1 to 30, further preferably 1 to 10, furthermore preferably 1 to 5, and most preferably 1 to 2.

In a more preferred embodiment of the invention, the protein described in (b) above is a protein comprising a modified amino acid sequence that has one or more conservatively substituted amino acid residues in the amino acid sequence (a) above and having saponin-decomposing activity.

The expression "conservatively substituted" herein means that one or more amino acid residues are substituted with other amino acid residues which are chemically homologous not to substantially alter the protein activity. For example, a hydrophobic residue is substituted with another hydrophobic residue or a polar residue is substituted with another polar residue having the same electric charge. Functionally homologous amino acids of different types, which can be conservatively substituted in this way, are known to the skilled in the art. Examples of such amino acids include non-polar (hydrophobic) amino acids such as alanine, valine, isoleucine, leucine, proline, tryptophan, phenylalanine, and methionine; polar (neutral) amino acids such as glycine, serine, threonine, tyrosine, glutamine, asparagine, and cysteine; positively charged (basic) amino acids such as arginine, histidine, and lysine; and further, negatively charged (acidic) amino acids such as aspartic acid, and glutamic acid.

In the present invention, the term "protein having saponin-decomposing activity" means a protein that is verified to have an activity to decompose saponin. For example it means a protein which is verified to have saponin-decomposing activity when measured under the same conditions as described in Example 5. This protein can be isolated and purified from "organisms having saponin-decomposing activity" described below.

A protein according to the present invention can be obtained, for example, as follows.

An organisms having saponin-decomposing activity is cultured and a protein having saponin-decomposing activity is isolated and purified from the resulting culture using the saponin-decomposing activity as an index. The amino acid sequence of the protein thus purified is analyzed, an oligonucleotide encoding this sequence is synthesized, and the PCR (polymerase chain reaction) is carried out using DNA of said organism as a template to synthesize a long probe. A DNA sequence of the translation region of the saponin-decomposing enzyme gene is analyzed by the inverse PCR or the RACE (rapid amplification of cDNA ends) method using this probe. The translation region of the saponin-decomposing enzyme thus obtained is linked to a regulatory sequence which functions in a host to be used for expression to obtain an expression vector. This expression vector is used to transform the host, the resulting transformant is cultured, and thus a saponin-decomposing enzyme can be obtained.

An "organism having saponin-decomposing activity" herein can be any organism having saponin-decomposing activity and is not particularly limited and includes microorganisms and plants. Examples of such microorganism include filamentous fungi that belong to genus *Neocosmospora*, genus *Aspergillus*, and genus *Eupenicillium*. These fungi are used in manufacturing soy sauce and soybean paste by fermentation and known to have saponin-decomposing activity. Further, said microorganisms include actinomycetes and bacteria since some of them may also have saponin-decomposing activity. Said plants include plant itself, plant cells, callus or culture cells derived from leguminous plants since some saponin glycotransferase of such plants may catalyze reverse reaction.

In a preferred embodiment of the present invention, a protein or a polynucleotide according to the present invention is derived from a microorganism, more preferably a microorganism belonging to filamentous fungus. A microorganism belonging to such filamentous fungus is preferably filamentous fungus belonging to genus *Neocosmospora*, genus *Aspergillus*, or genus *Eupenicillium*.

Examples of filamentous fungi that belong to genus *Neocosmospora* include *Neocosmospora vasinfecta* var. *vasinfecta* PF1225 (accession number: FERM BP-7475) and mutants thereof. Examples of filamentous fungi that belong to genus *Aspergillus* include *Aspergillus* sp. PF1224 (accession number: FERM BP-8004) and mutants thereof. Examples of filamentous fungi that belong to genus *Eupenicillium* include *Eupenicillium brefeldianum* PF1226 (accession number: FERM BP-7476) and mutants thereof.

Polynucleotide

The present invention provides a polynucleotide which encodes a protein of the present invention.

A polynucleotide according to the present invention is typically a polynucleotide selected from the group consisting of (i) to (iv) described above.

Namely, according to one embodiment of the present invention, the polynucleotide comprises a DNA sequence selected from the group consisting of the DNA sequences shown in SEQ ID NOs: 1, 3, and 5.

According to another embodiment of the present invention, the polynucleotide comprises a DNA sequence having at least 70% homology to the polynucleotide comprising the DNA sequence shown in SEQ ID NO: 1, 3, or 5 and encodes a protein having saponin-decomposing activity. The homology to the polynucleotide comprising the DNA sequence shown in SEQ ID NO: 1, 3, or 5 is preferably more than 80%, more preferably more than 90%, furthermore preferably more than 95%, or most preferably more than 98%.

Further, figures for homology shown in the present specification can be any figures calculated using a homology search program known to the skilled in the art. For example, figures can be readily calculated using default parameters in FASTA, BLAST, or the like.

According to another embodiment of the present invention, the polynucleotide comprises a DNA sequence having one or more bases deleted, substituted, inserted, or added in the DNA sequence shown in SEQ ID NO: 1, 3, or 5 and encodes a protein having saponin-decomposing activity.

Here, the number of amino acid residues that can be deleted, substituted, inserted, or added is preferably 1 to 50, more preferably 1 to 30, further preferably 1 to 10, furthermore preferably 1 to 5, and most preferably 1 to 2.

According to still another embodiment of the present invention, the polynucleotide hybridizes with a polynucleotide comprising the DNA sequence shown in SEQ ID NO: 1, 3, or 5 under stringent conditions and encodes a protein having saponin-decomposing activity. Further, according to the present invention, the polynucleotide also implies a polynucleotide which is complementary to a polynucleotide encoding a protein having saponin-decomposing activity.

The term "stringent conditions" herein means controlled conditions under which a probe comprising a DNA sequence partly or entirely encoding an amino acid sequence of a protein according to the present invention hybridized with a gene encoding a corresponding homologue while this probe does not hybridize with glucuronidase having a molecular weight described in Japanese Patent Publication No. 32714/1995. More specifically, for example, according to the method of ECL Direct DNA/RNA Labeling Detection System (Amersham) using the whole length of polynucleotide encoding the standardized amino acid sequence shown in SEQ ID NO: 1, 3, or 5 as a probe, pre-hybridization is first carried out for 1 hour (42° C.), after which said probe is added, hybridization (42° C.) is carried out for 15 hours, and then washing process is carried out first with a 0.5×SSC solution (SSC: 15 mM trisodium citrate, 150 mM sodium chloride) supplemented with 0.4% SDS and 6 M urea twice at 42° C. for 20 minutes and then with a 5×SSC solution twice at room temperature (about 25° C.) for 10 minutes.

Recombinant Vector

The present invention provides a recombinant vector comprising the abovementioned polynucleotide.

The procedure and method for constructing a recombinant vector according to the present invention can be any of those commonly used in the field of genetic engineering.

Examples of the expression vector as used herein include vectors which can be incorporated into a host chromosome DNA and vectors having a self-replicable autonomous replication sequence which can be present as a plasmid in a host cell, for example, pUC vectors (e.g., pUC18 and pUC118), pBluescript vectors (e.g., pBluescript II KS+), and plasmids such as pBR322 plasmid. One or more of copies of the gene can be present in a host cell.

A regulatory sequence for the recombinant vector can be any regulatory sequence which can function in a host and is not particularly limited. For example, a promoter, a terminator, and the like can be used. Such a regulatory sequence can be ligated to a gene encoding a protein having saponin-decomposing activity for the gene expression.

The ligation to a regulatory sequence can be carried out, for example, according to an ordinary method by inserting a translation region of a gene encoding a protein of interest (gene of interest) downstream of a promoter in the right direction. In this case, the protein can be expressed as a fusion protein by ligating the gene of interest to a foreign gene encoding a translation region of another protein.

The expressed protein having saponin-decomposing activity or the expressed fused protein having said activity can be produced in a host cell used for expression or released into a medium.

For example, a saponin-decomposing enzyme derived from *Neocosmospora vasinfecta* var. *vasinfecta* PF1225 (FERM BP-7475) was revealed to have a signal peptide sequence of 26 amino acid residues at the N-terminal side according to the DNA sequence analysis and N-terminal amino acid sequence analysis (see Example). Similarly, a saponin-decomposing enzyme derived from *Aspergillus* sp. PF1224 and a saponin-decomposing enzyme derived from *Eupenicillium brefeldianum* PF1226 were revealed to have signal peptide sequences of 28 amino acid residues and 17 amino acid residues at the N-terminal side, respectively.

Accordingly, for example, when filamentous fungi such as those belonging to genus *Trichoderma* and genus *Aspergillus* are used as a host, the protein can be released into a medium by utilizing a signal sequence included in this sequence.

Further, the saponin-decomposing enzyme derived from *Neocosmospora vasinfecta* var. *vasinfecta* PF1225 having a molecular weight of about 77 kDa is inferred to be glycoproteins from a molecular weight of about 68 kDa estimated from a deduced amino acid composition and a molecular weight of about 68 kDa of a protein expressed in strains of *Escherichia coli* and *Trichoderma viride*. Similarly, the saponin-decomposing enzyme derived from *Aspergillus* sp. PF1224 having a molecular weight of about 90 kDa is inferred to be glycoproteins from a molecular weight of about 65 kDa estimated from a deduced amino acid composition and a molecular weight of about 80 kDa of a protein expressed in strains of *Trichoderma viride*. Further, the saponin-decomposing enzyme derived from *Eupenicillium brefeldianum* PF1226 having a molecular weight of about 90 kDa is inferred to be glycoproteins from a molecular weight of about 65 kDa estimated from a deduced amino acid composition.

These sugar chain are presumed not to have great influence on the expression of activity. However, various modification after translation, such as addition of various sugar chains, can be carried out anticipating effective changes in heat resistance, optimum pH, stability during storage, or the like.

A recombinant vector according to the present invention can be constructed by further ligating a selective marker gene such as a drug resistance gene and/or a gene complementing a nutritional requirement.

A gene marker can be appropriately selected depending on the technique for selecting a transformant. For example, a gene encoding drug resistance or a gene complementing a nutritional requirement can be used. Examples of the drug resistance gene include genes conferring resistance to destomycin, benomyl, oligomycin, hygromycin, G418, pleomycin, bialaphos, blasticidin S, phleomycin, phosphinothricin, ampicillin, streptomycin, and kanamycin. Examples of the gene complementing a nutritional requirement include amdS, pyrG, argB, trpC, niaD, TRP1, LEU2, and URA3. Further, a gene marker can be a gene complementing a nutrient requirement indigenous to a host to be used for expression in systems for synthesizing various amino acids, vitamins, nucleic acids, or the like, or a gene complementing a nutrient requirement that is rendered by various mutagenic treatments.

Production of Transformant and Protein of Interest

The present invention provides a host transformed with the abovementioned recombinant vector.

A host to be used in the present invention is not particularly restricted and any organism which can properly transcript and translate a gene encoding a protein having saponin-decomposing activity can be used. Examples of the host include bacteria such as *Escherichia coli* and *Bacillus* spp., actinomycetes, yeasts, filamentous fungi such as *Trichoderma* spp. and mutants thereof.

A recombinant vector for the gene expression can be introduced into a host by an ordinary method. Examples of the method for the introduction include the electroporation method, the polyethylene glycol method, the aglobacterium method, the lithium method, and the calcium chloride method. A method effective to each host cell can be selected.

A transformant (transformed host cell) can be cultured according to an ordinary method by appropriately selecting a medium, culture conditions and the like.

Conventional components can be used in a medium. As a carbon source, glucose, sucrose, cellulose, starch syrup, dextrin, starch, glycerol, molasses, animal and vegetable oils, and the like can be used. As a nitrogen source, soybean powder, wheat germ, cornsteep liquor, cotton seed lees, bouillon, peptone, yeast extract, ammonium sulfate, potassium nitrate, urea, and the like can be used. If necessary, sodium, potassium, calcium, magnesium, cobalt, chlorine, phosphoric acid, sulfuric acid, and other inorganic salts that can produce ions, such as potassium chloride, magnesium sulfate, monopotassium phosphate, zinc sulfate, manganese sulfate, and copper sulfate, can be effectively added. If necessary, various vitamins, amino acids, trace nutrients such as nucleotides, and selective drugs such as antibiotics can be added. Further, organic and inorganic substances to promote the growth of transformants and enhance the expression of an introduced gene can be appropriately added.

Cultivation can be carried out in a medium selectively containing these components.

For example, in a liquid medium, the cultivation can be carried out using a culture method under an aerobic condition, a shaking culture method, an agitation culture method with aeration, a submerged culture method or the like. The pH of the medium is, for example, about 5 to 8. The cultivation can be carried out at a normal temperature, such as 14° C. to 40° C., preferably 26° C. to 37° C., for about 1 to 25 days.

In a method of producing a protein of interest according to the present invention, a gene expression product, namely the protein of interest having saponin-decomposing activity, can be obtained from the culture of transformed cells. The protein of interest can be obtained from the culture according to an ordinary method. For example, steps of the extraction from the culture (e.g., by mashing, and crushing under pressure), the recovery (e.g., by filtration and centrifugation), and/or the purification (e.g., by salting out and solvent precipitation) can be appropriately combined. Furthermore, in these steps, a protease inhibitor, such as phenylmethylsulfonyl fluoride (PMSF), benzamidine and leupeptin, can be added if necessary.

According to another embodiment of the present invention, it is also possible to express a gene encoding a protein having saponin-decomposing activity in a plant which produces saponins, such as plants of soybean, kidney bean, cowpea, pea, peanut, and broad bean, and alfalfa to generate a plant body containing soyasapogenol B, from which soyasapogenol B is directly obtained. In this case, actin, ubiquitin, cauliflower mosaic virus 35S promoter, or the like, or a regulatory sequence of a gene specifically expressed at a part, such as the seed, can be used.

A gene encoding a protein having saponin-decomposing activity is properly linked to such a regulatory sequence and further, a drug resistance gene conferring resistance to bialaphos, kanamycin, blasticidin S, or the like is linked if necessary. The resultant product can be introduced into a plant cell, for example, by a direct introduction method such as the particle-gun method, the PEG method, the electroporation method, and the microinjection method, or by an indirect introduction method using Ti plasmid vector of aglobacterium to generate a transformed plant cell. Introduction of the gene into a plant cell or plant body can be carried out according the method of Vaeck M. et al (Nature, 328, 33-37, 1987).

The plant cell thus transformed can be redifferentiated by the method known to the skilled in the art into a complete body of a transformed plant. Further, the transformed plant is cultivated and the resultant whole plants and/or organs, such as seeds, in which a gene encoding a protein having saponin-decomposing activity is expressed are harvested, from which soyasapogenol B can be obtained using a method suitable for its property, such as the solvent extraction method.

Production of Soyasapogenol B

Another embodiment of the present invention provides a method of producing soyasapogenol B which comprises decomposing a glycoside having soyasapogenol B as an aglycone using a culture containing a protein having saponin-decomposing activity which can be obtained from the abovementioned transformed host.

Further, still another embodiment of the present invention provides a method of producing soyasapogenol B which comprises decomposing a glycoside having soyasapogenol B as an aglycone using at least one kind of protein selected from the group consisting of the abovementioned protein and the protein which can be obtained from the abovementioned transformed host.

Examples of the "glycoside having soyasapogenol B as an aglycone" include soyasaponins I, II, III, IV, and V; azukisaponins II and V, astragaloside VIII, and sophoraflavoside I, which are primarily found in leguminous plants.

Examples of the substance containing a glycoside having soyasapogenol B as an aglycone include a substance extracted from soybeans or defatted soybeans (soybean cake) with hot water, alcohol or alcohol hydrate, or preferably a substance from which impurities such as proteins, sugars and lipids are removed by an ordinary method.

According to the present invention, soyasapogenol B can be obtained by allowing a culture containing a protein having saponin-decomposing activity, a protein according to the present invention or a protein obtained from a host according to the present invention to act on a substance containing a glycoside having soyasapogenol B as an aglycone and/or said glycoside.

More specifically, for example, about 1% to 10% by weight saponin (Koshiro Seiyaku) is dissolved in water or a buffer solution, such as an acetate buffer or a phosphate buffer, to which saponin-decomposing enzyme is added. The reaction is carried out at an appropriate temperature, for example 20° C. to 50° C., after which the resulting reaction solution is extracted with an organic solvent such as ethyl acetate to obtain soyasapogenol B.

EXAMPLES

The present invention is further illustrated by the following examples that are not intended as a limitation of the invention.

Reference Example 1

Confirmation of *Aspergillus* Saponin-Decomposing Enzyme

A PDA slant (about 1 cm$^2$) of *Aspergillus* sp. PF1224 (PERM BP-8004) was inoculated into 100 ml of a TS medium (2.0% soluble starch, 1.0% glucose, 0.5% polypeptone, 0.6% wheat germ, 0.3% yeast extract, 0.2% soybean grounds, and 0.2% calcium carbonate (pH 7.0 before sterilization)) dispensed into a 500-ml Erlenmeyer flask. Incubation was then carried out at 25° C. for 3 days with shaking. The resulting culture (4 ml) was inoculated into 100 ml of an MY medium (4% malt extract, 2.0% yeast extract, 0.2% potassium dihydrogenphosphate, 0.2% ammonium sulfate, 0.03% magnesium sulfate heptahydrate, 0.03% calcium chloride dihydrate (pH 7.0)) supplemented with 4.0% soybean saponin (Koshiro Seiyaku) dispensed into a 500-ml Erlenmeyer flask and incubation was then carried out for 3 days with shaking.

Saponin-decomposing activity shown in Test Example 1 was used as an index in the purification of saponin-decomposing enzyme derived from *Aspergillus* hereinafter.

The resulting culture (about 800 ml) was filtered with a glass filter (G3) and then centrifuged (8,000 rpm, 30 minutes) to remove cell debris. Ammonium sulfate (294 g) was added to about 570 ml of the supernatant thus obtained and the resulting precipitate was recovered by centrifugation (8,000 rpm, 30 minutes). This precipitate was dissolved in about 120 ml of a buffer solution A (0.1 M sodium acetate buffer, 1 M ammonium sulfate (pH 5.8)) and the resulting solution was subjected to hydrophobic chromatography using Butyl Toyopearl 650S (26 mm i.d.×330 mm) (Tosoh Co.). Elution was carried out with a concentration gradient from a buffer solution B (0.1 M sodium phosphate buffer-1 M ammonium sulfate (pH 5.8)) to 0.1 M sodium phosphate buffer (pH 5.8) and an unadsorbed fraction and a fraction eluted with an ammonium sulfate at a concentration from 1 M to 0.5 M were recovered.

Each of the recovered fractions was concentrated using Pellicon XL (cut-off molecular weight: 10,000) (Millipore), after which 1 M Tris-HCl buffer and ammonium sulfate were added to the concentrate so as to make their concentration the same as in a buffer solution C (50 mM Tris-HCl buffer, 1 M ammonium sulfate (pH 7.5)) and the resulting solution was subjected to hydrophobic chromatography using 6 ml of Resource PHE (Amersham Biosciences). Elution was carried out with a concentration gradient from the buffer solution C to the 50 mM Tris-HCl buffer solution (pH 7.5) and an unadsorbed fraction was recovered.

The fraction thus obtained was concentrated using Ultrafree 15 (cut-off molecular weight: 5,000) (Millipore) and then subjected to gel filtration chromatography using Superdex 200 pg (16 mm i.d.×600 mm) (Amersham Biosciences). Elution was carried out with a buffer solution D (25 mM sodium phosphate buffer, 0.15 M sodium chloride (pH 5.8)) and a fraction of a cut-off molecular weight of about 90 kDa was recovered.

SDS-PAGE was carried out with this fraction and a single band with an estimated molecular weight of about 90 kDa was observed.

Test Example 1

Measurement of Saponin-Decomposing Activity

An enzyme solution containing an enzyme of interest was desalted using a PD-10 column (Amersham Biosciences), after which an equal volume of 2% saponin solution was mixed and reaction was carried out at 37° C. for about 16 hours. The resulting reaction solution was extracted with an equal volume of ethyl acetate and the resulting extract was developed using TLC (solvent system used: chloroform:methanol=95:5). Utilizing color reaction of vanillin-sulfuric acid, soyasapogenol B having an Rf value of 0.35 was detected to measure enzyme activity of the enzyme solution of interest.

Test Example 2

Quantitative Analysis of Saponin-Decomposing Activity

A diluted enzyme solution was added to 50 µl of a 2% saponin solution to make a total volume of 100 µl and the resulting admixture was reacted for 30 minutes. Next, the resulting reaction solution was extracted with an equal volume of ethyl acetate and a 50 µl portion of the extract was diluted with 450 µof mobile phase. A 10 µl portion of the dilution was subjected to high performance liquid chromatography under the following conditions and a peak height at a retention time of about 7.5 minutes was measured. By comparing this height with that of authentic soyasapogenol B, saponin-decomposing activity of this enzyme was quantitatively evaluated.

Column: Inertsil ODS −2, 5 µm (4.6 mm i.d×250 mm)
Column temperature: 40° C.
Mobile phase: acetonitrile:methanol:water=50:35:15
Mobile phase flow rate: 0.8 ml/min Example 1

Isolation and Purification of Saponin-Decomposing Enzyme Derived from Genus *Neocosmospora* (SDN)

A PDA slant (about 1 cm$^2$) of *Neocosmospora vasinfecta* var. *vasinfecta* PF1225 (FERM BP-7475) was inoculated into 100 ml of a TS medium dispensed into a 500-ml Erlenmeyer flask. Incubation was carried out at 25° C. for 3 days with shaking. The resulting culture (4 ml) was inoculated into 100 ml of an MY medium supplemented with 4.0% soybean saponin (Koshiro Seiyaku) dispensed into a 500-ml Erlenmeyer flask and then incubation was carried out for 3 days with shaking.

Saponin-decomposing activity shown in Test Example 1 was used as an index in the purification of saponin-decomposing enzyme derived from genus *Neocosmospora* hereinafter.

The resulting culture (about 800 ml) was diluted with about 2 times volume of water and then centrifuged (8,000 rpm, 30 minutes) to remove cells. Ammonium sulfate (171 g) was added to the supernatant and the resulting precipitate was removed by centrifugation (8,000 rpm, 30 minutes). Further ammonium sulfate (573 g) was added to the resulting supernatant and the resulting precipitate was recovered by centrifugation (8,000 rpm, 30 minutes) and dissolved in 70 ml of a buffer solution C. The resulting solution was subjected to hydrophobic chromatography using Butyl Toyopearl 650S (26 mm i.d.×110 mm) (Tosoh Co.). Elution was carried out with a concentration gradient from a buffer solution C to 50 mM Tris-HCl buffer (pH 7.5) and an unadsorbed fraction was recovered.

Ammonium sulfate (about 239 g) was added to about 500 ml of this fraction and the resulting precipitate was recovered by centrifugation. The recovered precipitate was then dissolved in 4 ml of a buffer solution B and the resulting solution was subjected to hydrophobic chromatography using Phenyl Sepharose FF (16 mm i.d.×100 mm) (Amersham Biosciences). Elution was carried out with a concentration gradient from a buffer solution B to a 0.1 M sodium phosphate buffer solution (pH 5.8) and a fraction at an ammonium sulfate concentration of about 0.4 M was recovered.

The fraction thus recovered was subjected to gel filtration chromatography using Superdex 200 pg (16 mm i.d.×600 mm) (Amersham Biosciences). Elution was carried out with a buffer solution E (50 mM Tris-HCl buffer, 0.15 M sodium chloride (pH 7.5)) and a fraction of a cut-off molecular weight of about 76,000 was recovered.

SDS-PAGE was carried out with this fraction and a single band of an estimated molecular weight of about 77 kDa was observed.

Example 2

Amino Acid Sequence Analysis of Saponin-Decomposing Enzyme (SDN)

2a) Amino Acid Sequence of the N-Terminal Side

The fraction prepared as in Example 1 was subjected to SDS-PAGE and blotted onto a PVDF membrane (Immobilon-PSQ) (Millipore), after which the membrane was washed and dried in air. This was subjected to a protein sequencer model 492 (Applied Biosystems) to analyze the amino acid sequence.

The amino acid sequence obtained by the analysis was as follows:

N-terminal amino acid sequence: ASPPASVPNNPSSEE-ITLQ (SEQ ID NO: 7)

2b) Analysis of Inner Amino Acid Sequence (Peptide Mapping)

The fraction prepared in Example 1 was subjected to SDS-PAGE and the resultant proteins were stained using Coomassie Brilliant Blue R250. A single band stained at an estimated molecular weight of about 77 kDa was excised and destained using a 0.2 M ammonium bicarbonate buffer solution (pH 8.0) in 50% acetonitrile and dried at room temperature for about 2 hours in air.

Next, this gel strip was immersed in a 0.2 M ammonium bicarbonate buffer solution (pH 8.0) containing 0.02% Tween 20, after which trypsin (Promega) was added and reaction was carried out at 37° C. for 2 days. After the reaction, the supernatant was recovered and the gel strip was further washed 3 times with 60% acetonitrile and 0.1% trifluoracetic acid. The resulting washings and the reaction supernatant were combined, concentrated and subjected to a Model 172µ preparative HPLC system (Applied Biosystems) (RP-300 Aquiapore C18, 220×2.1 mm, with a concentration gradient from 0.1% trifluoracetic acid-35% acetonitrile to 0.085% trifluoracetic acid-35% acetonitrile). The following 5 polypeptides were fractionated.

| | | |
|---|---|---|
| Trp26.8: | LVFNPSPK | (SEQ ID NO: 8) |
| Trp27.59: | WNVAADGSGPSGEIR | (SEQ ID NO: 9) |
| Trp32.07: | VTILHNPEGVAPITAK | (SEQ ID NO: 10) |
| Trp39.43: | EHSDTIPWGVPYVPGSQ | (SEQ ID NO: 11) |
| Trp41.3: | LTDYSFDWYSDIR | (SEQ ID NO: 12) |

Example 3

Cloning and Sequence Analysis of Saponin-Decomposing Enzyme (SDN)

3a) Preparation of Long Probe Using PCR

A genomic DNA was prepared from cultured cells of *Neocosmospora vasinfecta* var. *vasinfecta* PF1225 (FERM BP-7475) to be used as a template for PCR.

The genomic DNA was isolated according to the method of Horiuchi et al. (J. Bacteriol., 170, 272-278, 1988). First, cells cultured in a TS medium were recovered by centrifugation (7,500 rpm, 10 minutes). The cells thus obtained were lyophilized, suspended in a TE solution (10 mM Tris-HCl buffer, 1 mM EDTA (pH 8.0)) and then treated in a 3% SDS solution at 60° C. for 30 minutes. Then TE-saturated phenol extraction was carried out to remove cell debris.

The extract was precipitated with ethanol and treated with Ribonuclease A (Nippon Gene) and Proteinase K (Wako Pure Chemical Industries, Ltd.), and the nucleic acid was then precipitated with 12% polyethylene glycol 6000. The precipitate was subjected to TE-saturated phenol extraction and ethanol precipitation, and the resulting precipitate was dissolved in a TE solution to obtain the genomic DNA.

Based on the peptide sequences obtained in Example 2, the following oligonucleotides encoding these sequences were synthesized and used as primers for PCR:

```
Primer N1:   CCIGCITCNGTNCCNAA   (SEQ ID NO: 13)

Primer N2:   CCIGCIAGYGTNCCNAA   (SEQ ID NO: 14)

Primer 2A:   CCRTCIGCNGCNACRTT   (SEQ ID NO: 15)

Primer 3A:   CCCCAIGGDATNGTRTC   (SEQ ID NO: 16)

Primer 4A:   ACICCYTCNGGRTTRTG   (SEQ ID NO: 17)
```

The PCR was carried out using Takara Taq (Takara Shuzo Co., Ltd.). The fragments were amplified by repeating 10 cycles of 30 seconds at 94° C., 30 seconds at 45° C., and 3 minutes at 55° C., after heat denaturation at 94° C. for 1 minute, followed by 20 cycles of 30 seconds at 94° C., 30 seconds at 47° C., and 3 minutes at 60° C. As a result, a specific fragment of about 0.8 kb was amplified in a combination of primer N1 and primer 4A. This fragment was cloned into pCR2.1-TOPO (pCR2.1-2) using a TOPO TA cloning kit (Invitrogen).

DNA sequence analysis was carried out using dRhodamine Terminator cycle sequencing ready reaction (Applied Biosystems) and ABI PRISM 310 genetic analyzer (Applied Biosystems). Decoding of the PCR product cloned in pCR2.1-2 revealed that this fragment was the amplification of the region from position 88 to position 812 of the sequence of SEQ ID NO: 1.

3b) Southern Analysis and Sequence Decoding Using Inverse PCR

In Southern analysis, a genomic DNA digested with EcoRI was subjected to agarose gel electrophoresis and then to blotting onto Hibond N+ (Amersham Biosciences). An ECF Random-Prime Labelling and Detection System (Amersham Biosciences) was used for hybridization and a Molecular Imager FX (Bio-Rad) was used for band detection.

A band of about 2 kb was detected when the PCR product obtained in 3a) in Example 3 was used as a probe.

Next, the genomic DNA was digested with EcoRI, and a fragment of about 2 kb was recovered and circularized using a DNA ligation kit ver. 2 (Takara Shuzo Co., Ltd.). Using the resulting loop as a template, the fragment was amplified using LA Taq (Takara Shuzo Co., Ltd.) with the following primers for inverse PCR by repeating 25 cycles of a serial step consisting of 30 seconds at 94° C., 30 seconds at 50° C., and 4.5 minutes at 72° C., after heat denaturation at 94° C. for 1 minute. This amplified fragment of about 2 kb was cloned using a TOPO TA cloning kit (Invitrogen) and its sequence was analyzed using primer walking.

```
Primer 1 for inverse PCR:
TGACGCTGATACCAACGGCG          (SEQ ID NO: 18)

Primer 2 for inverse PCR:
CTAGTGGCAGTATTGGACAG          (SEQ ID NO: 19)
```

3c) Determination of Translation Region Using 3' RACE and 5' RACE Methods

The translation region was determined by the 3' RACE and 5' RACE methods using cDNA as a template. cDNA was prepared as follows.

As described in Example 1, a one ml portion of the culture of *Neocosmospora vasinfecta* var. *vasinfecta* PF1225 (FERM BP-7475) cultured in a TS medium was inoculated into 100 ml of an MY medium supplemented with 1% soybean saponin dispensed into a 500-ml Erlenmeyer flask. After incubation at 25° C. for 32 hours with shaking, cells were filtered through a nylon mesh (50 μm) and the cells thus obtained were frozen with liquid nitrogen. The frozen cells were smashed with a mortar and pestle and the whole RNA was extracted from the smashed cells. The whole RNA was extracted using ISOGEN (Nippon Gene) according to the attached protocol. mRNA was purified from the whole RNA using Oligotex-dT30 <Super> (Roche Diagnostics) according to the attached protocol.

By applying a 5'/3' RACE kit (Roche Diagnostics) to this mRNA, 3' and 5' regions were amplified using 3' RACE and 5' RACE according to the attached protocol. In this case, in the 3' RACE method, AmpriTaq Gold (Applied Biosystems) was used in the primary PCR and PCR Supermix High Fidelity (Lifetech Oriental Co., Ltd.) was used in the secondary PCR. In the primary and secondary PCRs in the 5' RACE method, PCR Supermix High Fidelity (Lifetech Oriental Co., Ltd.) was used.

The sequences of 3' RACE- and 5' RACE-specific primers were as follows.

```
3' RACE specific primer for primary PCR:
CCCAGGCCTTTAAGGATGGC        (SEQ ID NO: 20)

3' RACE specific primer for secondary PCR:
CTAGTGGCAGTATTGGACAG        (SEQ ID NO: 19)

5' RACE specific primer for cDNA synthesis:
TGACGCTGATACCAACGGCG        (SEQ ID NO: 18)

5' RACE specific primer for primary PCR:
CTGCTTGAGGGTAATGGGCTC       (SEQ ID NO: 21)

5' RACE specific primer for secondary PCR:
ACAGACGCCGGAGGAGAAGCG       (SEQ ID NO: 22)
```

The translation region of the SDN gene shown in SEQ ID NO: 1 was thus determined. From the result in Example 2a), the N terminal of the mature protein of SDN amino acid sequence was found to be located at position 27 from Met of the translation initiation site.

The presence of introns in the translation region was confirmed by comparing DNA sequences of the genomic DNA and cDNA. It was revealed that no intron was present in this translation region.

Example 4

Expression of Saponin-Decomposing Enzyme (SDN) in *Escherichia coli*

PCR was carried out with primers for expression in *E. coli* shown below using the cDNA obtained in Example 3 as a template.

The translation region of the SDN gene was amplified using PCR Supermix High Fidelity (Lifetech Oriental Co., Ltd.) by repeating 25 cycles of a serial step consisting of 30 seconds at 94 C, 30 seconds at 50 C, and 2 minutes at 72 C, after denaturation at 94° C. for 1 minute. A fragment obtained by digesting the resulting product with restriction enzymes NdeI and BamHI was ligated to plasmid pET15b (Novagen, Inc.) digested with the same restriction enzymes, using a DNA ligation kit ver. 2 (Takara Shuzo Co., Ltd.). *E. coli* strain BL21 (DE3) was transformed using this product according to an ordinary method and colonies having ampicillin resistance were obtained.

```
N-terminal primer for E. coli expression:
GGGCATATGGCTTCTCCTCCTGCTTCTG         (SEQ ID NO: 23)

C-terminal primer for E. coli expression:
GGGGGATCCTTAAGTGCCGCTCTGAGGACTACG   (SEQ ID NO: 24)
```

Colonies obtained were used for the following experiment.

Cells taken from the colonies were inoculated into 50 ml of an LB medium containing 50 μg/ml ampicillin dispensed in a 250-ml Erlenmeyer flask and incubation was carried out at 37° C. overnight with shaking. A 2 ml portion of this culture was further inoculated into 50 ml of an LB medium containing 50 μg/ml ampicillin dispensed in a 250-ml Erlenmeyer flask and incubation was carried out at 37° C. for 3 hours with shaking. Isopropyl-β-D-thiogalactopyranoside was added to the resulting culture at a final concentration of 0.4 mM and incubation was carried out for 3 hours for induction.

Cells thus cultured were collected by centrifugation and suspended in a buffer solution F (50 mM Tris-HCl buffer, 2 mM EDTA (pH 8.0)), after which cells were again recovered by centrifugation. After freezing at −80° C., these cells were suspended in 5 ml of a buffer solution F, lysozyme and Triton X 100 were added at final concentrations of 100 μg/ml and 0.1%, respectively, and the resulting suspension was allowed to stand at room temperature for about 20 minutes. Under ice cold, the cells were disrupted by ultrasonic treatment twice at a 50% duty cycle for 30 seconds using Sonifier 450 (BRANSON) and cell debris were removed by centrifugation.

Saponin-decomposing activity was measured according to Test Example 1 for the cell extract thus obtained as a crude enzyme solution.

As a result, a spot of the decomposed product, soyasapogenol B, was observed on TLC only for the extract of the cells in which the translation region of the saponin-decomposing enzyme was cloned.

Example 5

Expression of Saponin-Decomposing Enzyme (SDN) in *Trichoderma viride*

5a) Construction of Vector for Transformation

PCR was carried out as described in Example 4 with primers for expression in *Trichoderma* shown below using the cDNA obtained in Example 3 as a template.

A fragment obtained by digesting the resulting PCR product with restriction enzymes SmaI and PstI was ligated to plasmid pCB1-M2 (see Example 5 of WO 98/11239) digested with StuI and PstI, using a DNA ligation kit ver. 2 (Takara Shuzo Co., Ltd). The product was digested with XbaI, dephosphorylated and then linked to an XbaI cassette of the pyr4 gene derived from *Neurospora crassa* to construct pCB-SBe (FIG. 1).

```
N-terminal primer for expression in Trichoderma:
                                     (SEQ ID NO: 25)
GGGCCCGGGGCGCATCATGCACTTCTTTGACAAAGCGAC C-terminal primer for expression in Trichoderma:
                                     (SEQ ID NO: 26)
GGGCTGCAGTTAAGTGCCGCTCTGAGGACT
```

The XbaI cassette of the pyr4 gene was constructed as follows.

pFB6 (Biochem. Biophys. Res. Commun., 112, 284-289, 1983) was first digested with BGIII and then partially digested with HindIII to recover a fragment of about 1.9 kb. This fragment was ligated to pLITMUS28 (New England Biolabs) digested with BglII and HindIII. Next, the product was digested with BglII, blunted using a DNA blunting kit (Takara Shuzo Co., Ltd.), and then linked to a phosphorylated linker pXbaI (Takara Shuzo Co., Ltd.) to construct the XbaI cassette of the pyr4 gene.

5b) Acquisition of Uracyl-Requiring Strain Derived from *Trichoderma viride*

A spore suspension of *Trichoderma viride* MC300-1 (about $1.0 \times 10^9$ CFU/ml) was exposed to 2 UV lights at a distance of 30 cm with gentle mixing. The suspension was spread on a selective medium and incubated at 28° C. for 7 days and then grown strains were selected.

A selective medium used was a minimum medium (0.2% potassium dihydrogenphosphate, 0.4% ammonium sulfate, 0.03% urea, 0.03% magnesium sulfate heptahydrate, 0.03% calcium chloride, 0.5% glucose, 2.5% agar, 0.01% trace elements (5 mg of ion sulfate heptahydrate, 1.56 mg of manganese sulfate heptahydrate, 1.4 mg of zinc sulfate heptahydrate, and 2.0 mg of cobalt chloride dissolved in 1 L of water) supplemented with 10 μg/ml uridine and 1.0 mg/ml 5-fluoroorotic acid.

5c) Transformation of *Trichoderma viride* and Detection of Saponin-Decomposing Activity of Each Recombinant Cells of the uracyl-requiring *Trichoderma viride* strain obtained in 5b) of Example 5 were inoculated into 50 ml of a cell forming medium (1.0% yeast extract, 1.0% molt extract, 2.0% polypeptone, 2.5% glucose, 0.1% potassium dihydrogenphosphate, 0.05% magnesium sulfate heptahydrate, (pH 7.0 before sterilization)) dispensed in a 200-ml Erlenmeyer flask and incubation was carried out at 28° C. for 2 days with shaking. Mycelia were recovered from the resultant culture by centrifugation. Next, protoplasts were prepared from the mycelia, after which a DNA solution of plasmid pCB-SBe was added to carry out transformation (see Example 7 of WO 98/11239).

Further, in regeneration of transformants, 0.5 M sucrose was added to the minimum medium. Grown colonies were again inoculated onto the minimum medium and colonies grown in the medium were recognized as transformants.

Plasmid pCB-SBe was introduced into the uracyl-requiring *Trichoderma viride* strain. As a result, 3 transformants per 1 μg of pCB-SBe were obtained. Each of the transformants, 25 strains, was cultured (see Example 1 of WO 98/11239) and the resultant culture supernatant was subjected to SDS-PAGE, on which a band showing a molecular weight of about 68 kDa was observed only for the transformants.

Saponin-decomposing activity was measured according to Test Example 1 for this culture supernatant. As a result, a spot of the decomposed product, soyasapogenol B, was observed on TLC. On the other hand, this spot was not observed for the parent strain, the uracyl-requiring *Trichoderma viride*.

5d) Purification of Recombinant Saponin-Decomposing Enzyme (Recombinant SDN), and Comparison of Its Activity with Wild-Type Saponin-Decomposing Enzyme Derived from *Neocosmospora vasinfecta* var. *vasinfecta* PF1225 (Wild-Type SDN)

The culture obtained in 5c) of Example 5 (about 700 ml) was centrifuged (8,000 rpm, 30 minutes) to remove cell debris. Ammonium sulfate (64 g) was added to about 560 ml of the supernatant thus obtained and the resulting precipitate was removed by centrifugation (8,000 rpm, 30 minutes). Further, 74 g of ammonium sulfate were added to about 600 ml of the resultant supernatant and the resultant precipitate was recovered. To this precipitate were added 100 ml of 0.05 M Tris-HCl buffer (pH 7.5) and 16 g of ammonium sulfate and the admixture was subjected to hydrophobic chromatography using Butyl Toyopearl 650S (26 mm i.d.×330 mm) (Tosoh Co.). Elution was carried out with a concentration gradient from a buffer solution C to 50 mM Tris-HCl buffer (pH 7.5) and an unadsorbed fraction and a fraction eluted at an ammonium sulfate concentration from 1 M to 0.6 M were recovered.

Each of the fraction thus obtained was concentrated using Pellicon XL (cut-off molecular weight: 10,000) (Millipore). To about 8 ml of this concentrate were added 1.3 g of ammonium sulfate and 2 ml of 0.5 M sodium phosphate buffer (pH 5.8) and the admixture was subjected to hydrophobic chromatography using 6 ml of Resource PHE (Amersham Biosciences). Elution was carried out with a concentration gradient from a buffer solution B to 0.1 M sodium phosphate buffer (pH 5.8) and an unadsorbed fraction was recovered.

The fraction thus obtained was concentrated using Ultrafree 15 (cut-off molecular weight: 5,000) (Millipore). This concentrate was subjected to gel filtration chromatography using Superdex 200 pg (16 mm i.d.×600 mm) (Amersham Biosciences). Elution was carried out with a buffer solution G (50 mM sodium phosphate buffer, 0.15 M sodium chloride (pH 7.0)) and a fraction of a cut-off molecular weight of about 68,000 was recovered.

SDS-PAGE was carried out with this fraction and a single band with an estimated molecular weight of about 68 kDa was observed.

The optimum pH and the optimum temperature for the recombinant saponin-decomposing enzyme thus purified (occasionally referred to as "recombinant SDN" hereinafter) and the saponin-decomposing enzyme purified in Example 1 (occasionally referred to as "wild-type SDN" hereinafter) were measured according to Test Example 2.

In measuring the optimum pH, first, to 50 μl of a 2% saponin solution were added 20 μl each of 0.5 M individual buffer solutions (sodium acetate buffer (pH 4.5, pH 5.0, pH 5.8); sodium phosphate buffer (pH 5.0, pH 5.8, pH 7.0) and Tris-HCl buffer (pH 7.0, pH 8.0, pH 9.0)) and a diluted enzyme solution to make a total volume of 100 μl. Reaction was carried out at 37° C. for 30 minutes, and then the amount of soyasapogenol B produced was measured.

Figure 2:
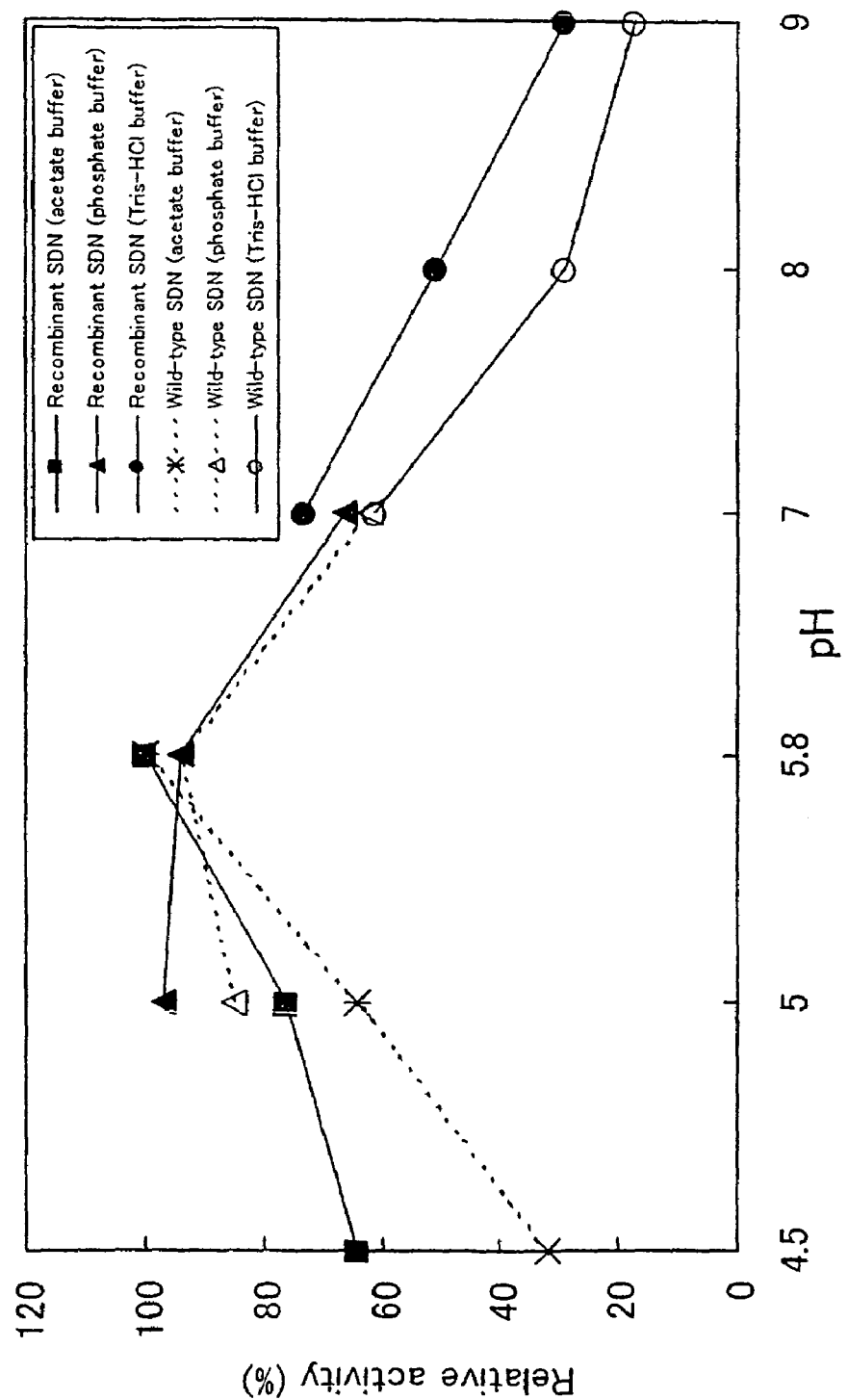
FIG. 2 shows the optimum pH for recombinant saponin-decomposing enzymes in Example 5. In the Figure, the wild-type SDN means the saponin-decomposing enzyme derived from *Neocosmospora vasinfecta* var. *vasinfecta* PF1225, and the recombinant SDN means the recombinant saponin-decomposing enzyme.

Results are shown in FIG. 2.

In measuring the optimum temperature, first, to 50 μl of a 2% saponin solution were added 20 μl of 0.5 M sodium phosphate buffer (pH 5.8) and a diluted enzyme solution to make a total volume of 100 μl. Reaction was carried out at each specified temperature for 30 minutes, and then the amount of soyasapogenol B produced was measured.

Figure 3:
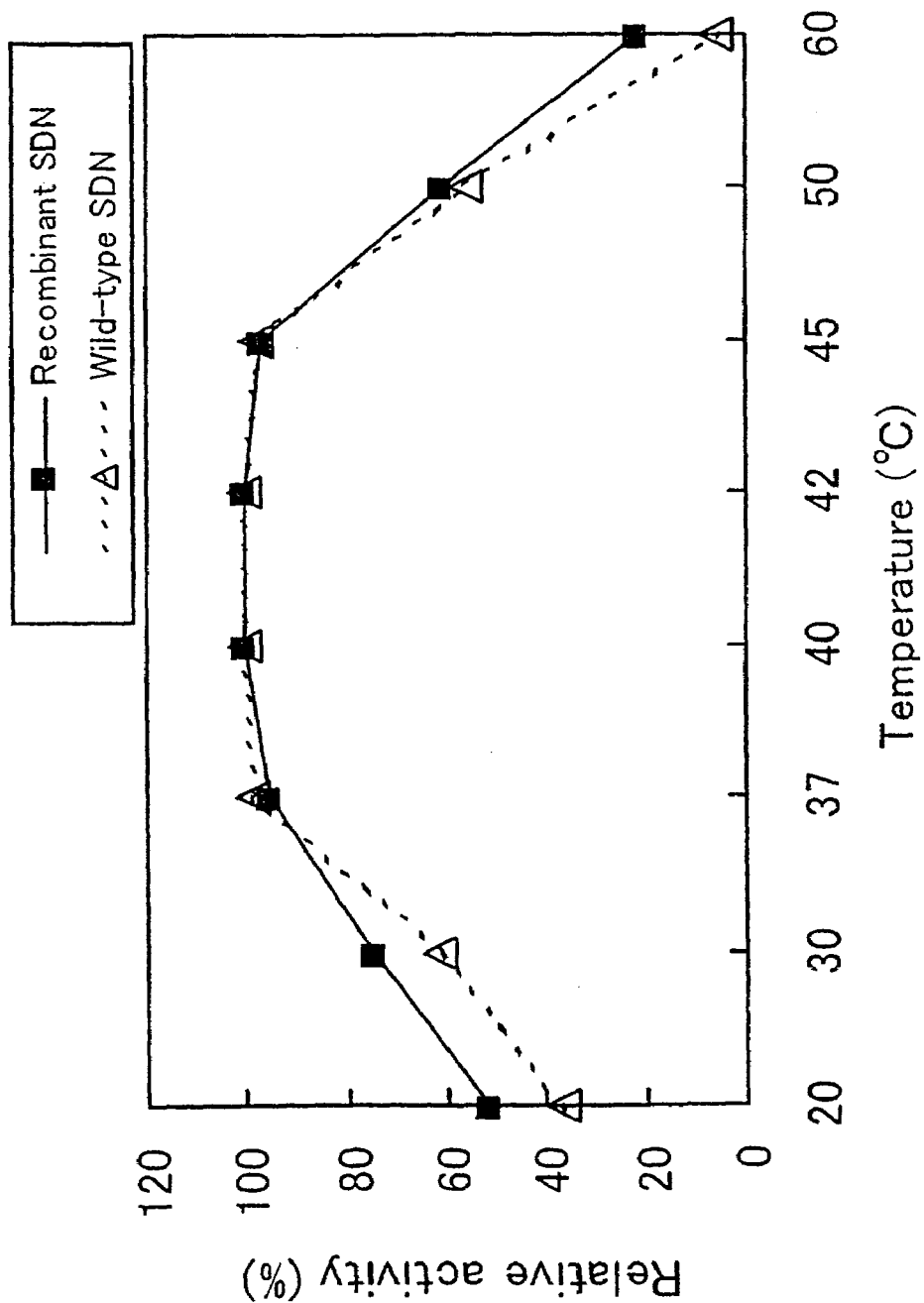
FIG. 3 shows the optimum temperature for recombinant saponin-decomposing enzymes in Example 5. In the Figure, the wild-type SDN means the saponin-decomposing enzyme derived from *Neocosmospora vasinfecta* var. *vasinfecta* PF1225, and the recombinant SDN means the recombinant saponin-decomposing enzyme.

Results are shown in FIG. 3.

As evident from these results, there was not much difference in activity although there was some difference in the molecular weight determined by SDS-PAGE.

Example 6

Amino Acid Sequence Analysis for Saponin-Decomposing Enzyme Derived from *Aspergillus* sp. PF1224 (SDA)

Saponin-decomposing enzyme purified from *Aspergillus* sp. PF1224 (FERM BP-8004) (SDA) (Reference Example 1) was fragmented as described in 2b) of Example 2 after excising a band of about 90 kDa, and subjected to HPLC as described in 2b) in Example 2 to fractionate the following 4 kinds of peptides.

```
Trp23.67:   LYNPDSPQPISAK        (SEQ ID NO: 27)

Trp24.0s:   LQFNPAPK             (SEQ ID NO: 28)

Trp38.05:   VDWFSDLTSTGQVTGSK    (SEQ ID NO: 29)

Trp24.5:    GEVSGSASVSIIHD       (SEQ ID NO: 30)
```

Example 7

Cloning and Sequence Analysis of SDA Gene

7a) Preparation of Long Probe Using PCR

A genomic DNA was isolated from cells cultured as described in Reference Example 1, as described in Example 3.

Based on the peptide sequences obtained in Example 6, the following oligonucleotides encoding these sequences were synthesized and used as primers for PCR.

```
Primer 23.67s1:  TAYAAYCCIGAYTCNCC   (SEQ ID NO: 31)

Primer 23.67s2:  TAYAAYCCNGAYAGYCC   (SEQ ID NO: 32)

Primer 24.0s:    CARTTYAAYCCIGCNCC   (SEQ ID NO: 33)

Primer 24.0a:    GGIGCNGGRTTRAAYTG   (SEQ ID NO: 34)

3 Primer         AARTCNGARAACCARTC   (SEQ ID NO: 35)
38.05a1:

Primer           AARTCRCTRAACCARTC   (SEQ ID NO: 36)
38.05a2:
```

The PCR was carried out as described in 3a) in Example 3. As a result, a fragment of about 1 kb was specifically amplified in a combination of primer 24.0 s and primer 38.05a1 among the primers above, which was then cloned into pCR2.1-TOPO using a TOPO TA cloning kit (Invitrogen) (pSDAPCR1).

Results of sequence analysis revealed that the fragment cloned into pSDAPCR1 was the amplification of the region from position 709 to position 1748 of the sequence of SEQ ID NO: 3.

7b) Southern Analysis and Screening using *E. coli* Colony Library

In Southern analysis, a genomic DNA previously digested with BamHI, EcoRI, and HindIII was subjected to agarose gel electrophoresis and then to blotting onto Hibond N+ (Amersham Bioscience). An ECF Random-Prime Labelling and Detection System (Amersham Bioscience) was used for hybridization and a Molecular Imager FX (Bio-Rad) was used for band detection.

Bands for a BamHI fragment of about 10 kb, an EcoRI fragment of about 20 kb, and a HindIII fragment of about 5 kb were detected when the PCR products obtained in 7a) above were used as a probe.

Next, the genomic DNA was digested with HindIII, and fragments of about 4 kb to 6 kb were recovered. The product was then linked to pUC18, which was previously digested with HindIII and dephosphorylated, to transform an *E. coli* strain DH5α. This *E. coli* was grown on an LB agar medium supplemented with ampicillin for colony formation, about 1,000 colonies thus obtained were blotted onto Hibond N+ (Amersham Bioscience). Here, one kind of positive clone (pSDAHind5/18) was obtained using the PCR product obtained in the abovementioned 7a) as a probe. This clone contained a HindIII fragment of about 5 kb.

7c) Determination of Translation Region Using 3' RACE and 5' RACE Methods

As described in 3c) in Example 3, the whole RNA was extracted from culture cells of *Aspergillus* sp. PF1224 (FERM BP-8004) prepared in Reference Example 1 and further, mRNA was isolated using a QuickPrep mRNA purification kit (Amersham Bioscience) according to the attached protocol.

By applying a 5'/3' RACE kit (Roche Diagnostics) to this mRNA, 3' and 5' regions were amplified. LA Taq (Takara Shuzo Co., Ltd.) was used for each PCR.

Sequences of 3' RACE- and 5' RACE-specific primers were as follows.

```
3' RACE specific primer for primary PCR:
CCTCGATACCCGAGGGACCG        (SEQ ID NO: 37)

3' RACE specific primer for secondary PCR:
GATGGGTTGCATGTTATCGC        (SEQ ID NO: 38)

5' RACE specific primer for cDNA synthesis:
GCGATAACATGCAACCCATC        (SEQ ID NO: 39)

5' RACE specific primer for primary PCR:
GACCACCTGGTTCAGTGGTG        (SEQ ID NO: 40)

5' RACE specific primer for secondary PCR:
GGGTTATAGAGTCTGGTAACG       (SEQ ID NO: 41)
```

The translation region of the SDA gene shown in SEQ ID NO: 3 was thus determined. The SDA protein purified as Reference Example 1 was analyzed for the mature N-terminal amino acid sequence in the same manner as described in Example 2a). As a result, the N terminal of the mature protein of SDA amino acid sequence was found to be located at position 29 from Met of the translation initiation site. Further, the presence of introns in the translation region was confirmed by comparing DNA sequences of the genomic DNA and cDNA. It was revealed that no intron was present in this translation region.

Example 8

Expression of Saponin-Decomposing Enzyme Derived from *Aspergillus* sp. PF1224 (SDA) in *Trichoderma viride*

8a) Construction of Vector for Transformation

First, PCR was carried out as described in Example 4 with primers for expression in *Trichoderma* shown below using pSDAHind5/18 obtained in Example 7b as a template.

Figure 4:
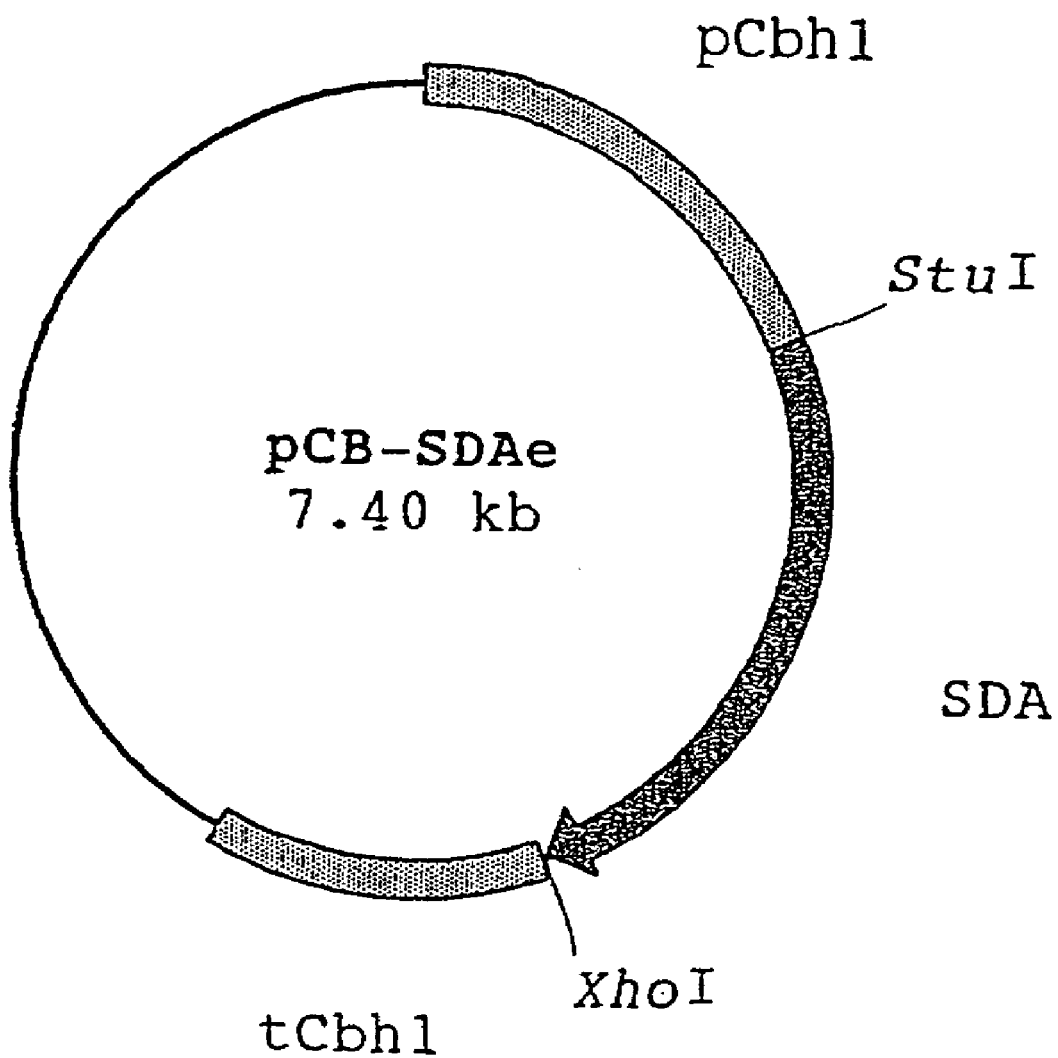
FIG. 4 shows the construction and restriction map for plasmid pCB-SDAe.

A fragment obtained by digesting the resulting PCR product with restriction enzymes StuI and XhoI was ligated to plasmid pCB1-M2 (see Example 5 of WO 98/11239) previously digested with StuI and XhoI using a DNA ligation kit ver. 2 (Takara Shuzo Co., Ltd.) to construct pCB-SDAe (FIG. 4)

```
N-terminal primer for SDA expression in
Trichoderma:
                            (SEQ ID NO: 42)
GGGAGGCCTGCGCATCATGCATGTTGTCGCAAGTACCAC C-terminal primer for SDA expression in
Trichoderma:
                            (SEQ ID NO: 43)
GGGCTCGAGTACCTCAAGTCCCATTTGCCGGCTGC
```

8b) Transformation of *Trichoderma viride* and Detection of Saponin-Decomposing Activity of Each Recombinant A host, the uracyl-requiring *Trichoderma viride* strain obtained in 5b) in Example 5, was transformed by the co-transformation method using pCB-SDAe and vector pPYR4 in which the pyr4 cassette was ligated to pLITMUS28 (see 5a) in Example 5), as described in 5c) in Example 5. As a result, about 12 strains of transformants per 1 μg of DNA were obtained.

Each of the transformants thus obtained was cultured (see Example 1 of WO 98/11239) and the resultant culture supernatant was subjected to SDS-PAGE, on which a band showing a molecular weight of about 80 kDa was observed only for the transformants.

Saponin-decomposing activity was measured using this culture supernatant as described in Test Example 1. As a result, a spot of the decomposed product, soyasapogenol B, was observed on TLC.

8c) Purification of Recombinant Saponin-Decomposing Enzyme Derived from *Aspergillus* sp. PF1224 (Recombinant SDA), and Comparison of Its Activity with Wild-Type Saponin-Decomposing Enzyme Derived from *Aspergillus* sp. PF1224 (Wild-Type SDA)

The culture obtained in 8b) above (about 600 ml) was centrifuged (8,000 rpm, 30 minutes) to remove cell debris. Ammonium sulfate (57 g) was added to about 500 ml of the supernatant thus obtained and the resulting precipitate was removed by centrifugation. Further, 64 g (40% saturation fraction) and then 70 g (60% saturation fraction) of ammonium sulfate were added to this supernatant and the resultant precipitate was dissolved in a 0.1 M sodium phosphate buffer solution (pH 5.8). To the 60% saturation fraction was added ammonium sulfate to make a final concentration of 1M, and then the admixture was subjected to hydrophobic chromatography using Butyl Toyopearl 650S (26 mm i.d.×250 mm) (Tosoh Co.). Elution was carried out with a concentration gradient from a buffer solution A to a 0.1 M sodium phosphate buffer solution (pH 5.8) and a fraction eluted at an ammonium sulfate concentration from 0.9 M to 0.2 M was recovered.

The fraction thus obtained was concentrated using Pellicon XL (cut-off molecular weight: 10,000) (Millipore) and Ultrafree 15 (cut-off molecular weight: 10,000) (Millipore), desalted using a PD-10 column (Amersham Bioscience) and then subjected to ion-exchange chromatography using 6 ml of Resource Q (Amersham Bioscience). Elution was carried out with a concentration gradient from 50 mM Tris-HCl buffer (pH 7.5) to 50 mM Tris-HCl buffer-0.5 M sodium chloride (pH 7.5), and an unadsorbed fraction and a fraction eluted at a salt concentration of 0.08 M were recovered.

The fraction thus obtained was concentrated using Ultrafree 15 (cut-off molecular weight: 10,000) (Millipore) and then subjected to gel filtration chromatography using Superdex 200 pg (16 mm i.d.×600 mm) (Amersham Bioscience). Elution was carried out with a buffer solution G and a fraction of a cut-off molecular weight of about 50 kDa was recovered.

SDS-PAGE was carried out with this fraction and a single band with an estimated molecular weight of about 80 kDa was observed. Further, the cut-off molecular weight on the gel filtration and the molecular weight on the SDS-PAGE were different probably because this protein was adsorbed unspecifically to the carriers.

The optimum pH and the optimum temperature were measured for the recombinant SDA thus purified and the saponin-decomposing enzyme purified in Reference Example 1 (wild-type SDA), according to Test Example 2.

The optimum pH and the optimum temperature were measured as described in 5d) in Example 5.

Figure 5:
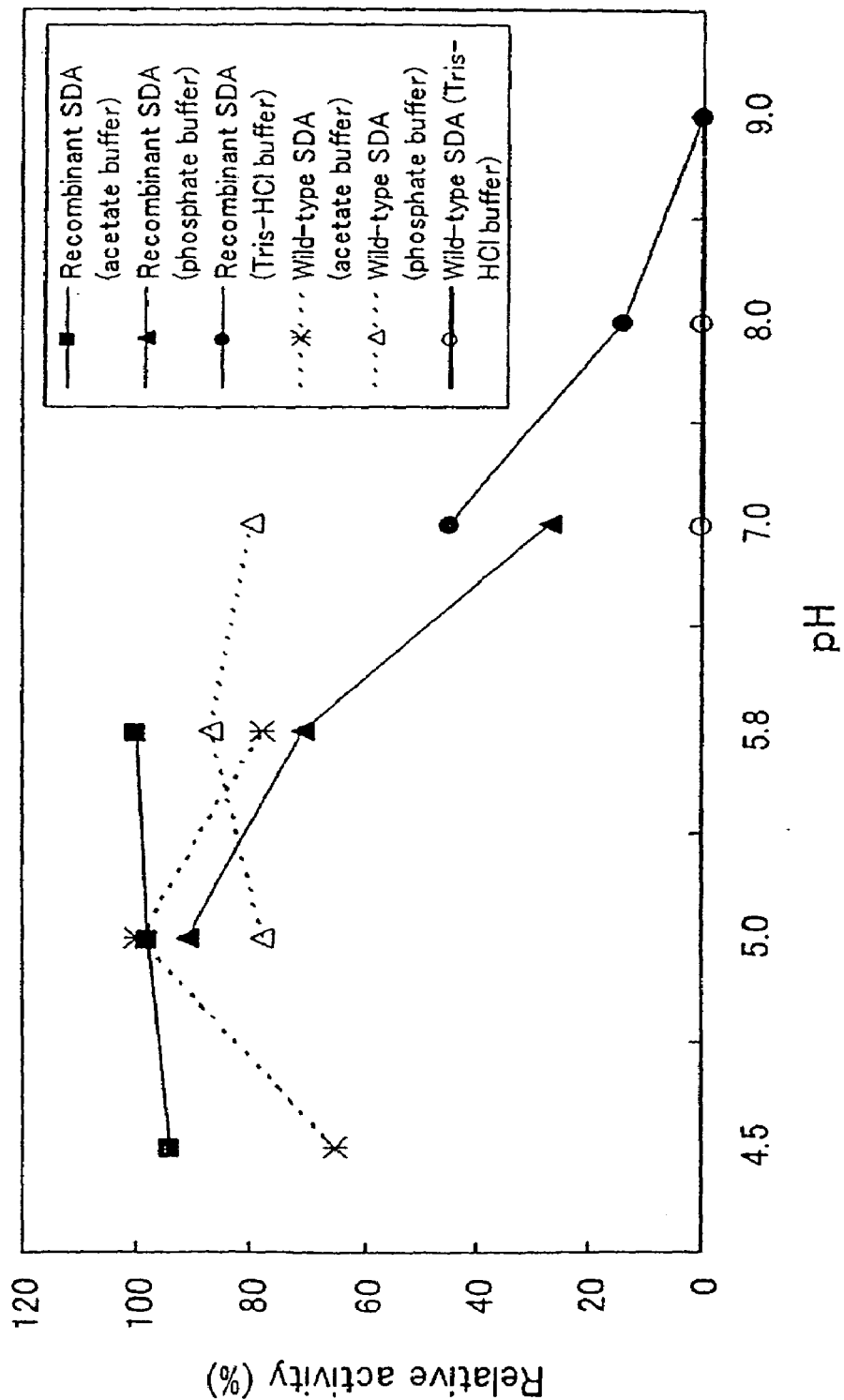
FIG. 5 shows the optimum pH for recombinant saponin-decomposing enzymes in Example 8. In the Figure, the wild-type SDA means the saponin-decomposing enzyme derived from *Aspergillus* sp. PF1224, and the recombinant SDA means the recombinant saponin-decomposing enzyme.
Figure 6:
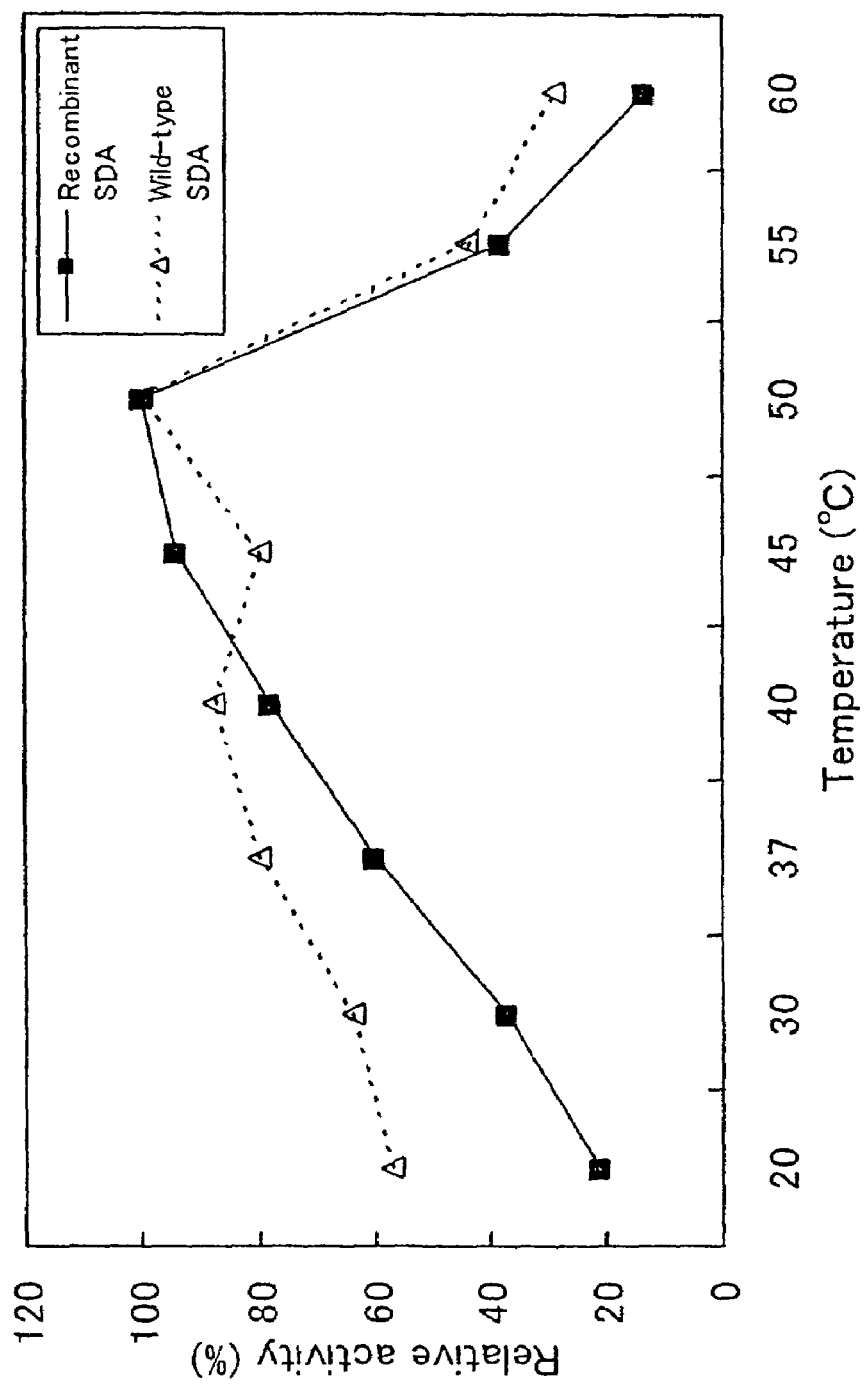
FIG. 6 shows the optimum temperature for recombinant saponin-decomposing enzymes in Example 8. In the Figure, the wild-type SDA means the saponin-decomposing enzyme derived from *Aspergillus* sp. PF1224, and the recombinant SDA means the recombinant saponin-decomposing enzyme.

Results are shown in FIGS. 5 and 6.

As a result, it was revealed that although the recombinant SDA exhibited lower specific activity in sodium phosphate buffer at pH 7 as compared to the wild-type SDA, it exhibited improved specific activity in Tris-HCl buffer and at high pHs.

Example 9

Isolation and Purification of Saponin-Decomposing Enzyme Derived from *Eupenicillium brefeldianum* PF1226 (SDE)

A PDA slant (about 1 cm²) of *Eupenicillium brefeldianum* PF1226 (FERM BP-7476) was inoculated into 100 ml of a TS medium dispensed into a 500-ml Erlenmeyer flask and then incubation was carried out at 25° C. for 3 days with shaking. The resulting culture (4 ml) was inoculated into 100 ml of an MY medium supplemented with 1.0% soybean saponin (Koshiro Seiyaku) dispensed into a 500-ml Erlenmeyer flask and then incubation was carried out for 7 days with shaking.

The resulting culture (about 1,000 ml) was filtered with a glass filter (G3) to remove cell debris. Ammonium sulfate (73 g) was added to this culture supernatant (about 640 ml) and the resulting precipitate was removed by centrifugation (8,000 rpm, 30 minutes). Further, ammonium sulfate (256 g) was added to the resulting supernatant (about 670 ml) and the resulting precipitate was recovered by centrifugation. This precipitate was dissolved in about 50 ml of 0.1 M sodium acetate buffer (pH 5.8), 13.2 g of ammonium sulfate was added, and then water was added to make a final concentration of 1 M ammonium sulfate-0.1M sodium acetate buffer.

After centrifugation, this solution was subjected to hydrophobic chromatography using Butyl Toyopearl 650S (26 mm i.d.×330 mm) (Tosoh Co.). Elution was carried out with a concentration gradient from a buffer solution C to 50 mM Tris-HCl buffer and a fraction eluted at an ammonium sulfate concentration of 0.7 M to 0.5 M was recovered.

The recovered fraction was concentrated using Pellicon XL (cut-off molecular weight: 10,000) (Millipore), after which sodium phosphate buffer and ammonium sulfate were added to make the concentrate having the same component as the buffer solution A and the resulting solution was subjected to hydrophobic chromatography using 6 ml of Resource PHE (Amersham Bioscience). Elution was carried out with a concentration gradient from a buffer solution A to a 0.1 M sodium phosphate buffer solution (pH 5.8) and a fraction eluted from an ammonium sulfate concentration of 1 M to 0.3 M was recovered.

This fraction was concentrated using Ultrafree 15 (cut-off molecular weight: 10,000) (Millipore), desalted using a PD-10 column (Amersham Bioscience) and then subjected to ion-exchange chromatography using 6 ml of Resource Q (Amersham Bioscience). Elution was carried out with a concentration gradient from 20 mM sodium phosphate buffer (pH 7.0) to 20 mM sodium phosphate buffer-1 M sodium chloride (pH 7.0), and an unadsorbed fraction was recovered.

The fraction thus obtained was concentrated using Ultrafree 15 (cut-off molecular weight: 10,000) (Millipore) and then subjected to gel filtration chromatography using Superdex 200 pg (16 mm i.d.×600 mm) (Amersham Bioscience). Elution was carried out with a buffer solution G and a fraction of a cut-off molecular weight of about 90 kDa was recovered.

SDS-PAGE was carried out with this fraction and a single band with an estimated molecular weight of about 90 kDa was observed.

Example 10

Analysis of Amino Acid Sequence of SDE

10a) Amino Acid Sequence of N-Terminal Side

The N-terminal side amino acid sequence of the fraction prepared in Example 9 was analyzed as described in 2a) in Example 2. As a result, the following amino acid sequence was obtained.

N-terminal amino acid sequence: STTPAPPQPEPI (SEQ ID NO: 44)

10b) Peptide Mapping

The SDE purified in Example 9 was fragmented after excising a band of about 90 kDa, as described in 2b) in Example 2. The fragments were subjected to HPLC as described in 2b) in Example 2 and the following 3 kinds of peptides were fractionated.

Trp20.73: ADPAFSPDGTR (SEQ ID NO: 45)

Trp34.21: LHPDDTHMGWSSF (SEQ ID NO: 46)

Trp36.26: GFSGAGDEILYIGSTR (SEQ ID NO: 47)

Example 11

Cloning and Sequence Analysis of SDE Gene

11a) Preparation of Long Probes Using PCR

The genomic DNA was isolated from the cells cultured in Example 9, as described in Example 3.

Based on the sequences of the peptides obtained in Example 10, the following oligonucleotides encoding these sequences were synthesized and used as primers for PCR.

```
Primer Ns:      CCICARCCNGARCCNAT  (SEQ ID NO: 48)

Primer 20.37a:  CTRAAIGCNGGRTCNGC  (SEQ ID NO: 49)

Primer 34.21a:  CCANCCCATRTGNGTRTC (SEQ ID NO: 50)
```

The PCR was carried out as described in 3a) in Example 3.

As a result, a fragment of about 1 kb was specifically amplified with a combination of primer Ns and primer 20.73a among the primers above. This fragment was cloned into pCR2.1-TOPO using a TOPO TA cloning kit (Invitrogen) (pSDEPCR5).

Results of sequence analysis revealed that the fragment cloned into pSDEPCR5 was the amplification of the region from position 70 to position 1247 of the sequence of SEQ ID NO: 5.

11b) Screening Using Southern Analysis and Phage Library

In Southern analysis, a genomic DNA digested with PstI, SphI and XhoI was subjected to agarose gel electrophoresis and then to blotting onto Hibond N+ (Amersham Bioscience). An ECF Random-Prime Labelling and Detection System (Amersham Bioscience) was used for hybridization and a Molecular Imager FX (Bio-Rad) was used for band detection.

Bands of a PstI fragment of about 3 kb, an SphI fragment of about 4 kb, and an XhoI fragment of about 6 kb were detected when the PCR product obtained in 11a) above was used as a probe.

Next, the genomic DNA was partially digested with Sau3A1. The resultant product was then linked to λEMBL3/BamHI vector (Stratagene) and packaged using a MaxPlax packaging extract kit (Epicentre Technologies). The resultant phage library (about $5 \times 10^4$ PFU) was blotted onto Hibond N+ (Amersham Bioscience) and then 5 kinds of positive clones were obtained using the PCR fragment cloned in pSDEPCR5 as a probe, according to a DIG Hi-Prime DNA Labelling and Detection Kit (Roche Diagnostics). Of these clones, a XhoI fragment was recovered from a phage DNA containing the 6 kb XhoI fragment and cloned into pBluescript. II KS+ (pSDEXho/IIKS+1).

The DNA sequence of the SDE translation region was determined as shown in SEQ ID NO: 5 by the transposon method using pSDEXho/IIKS+1 as a template.

As a result of Example 10a), the N terminal of the mature protein of SDE amino acid sequence was found to be located at position 18 from Met of the translation initiation site.

The presence of introns in the translation region was confirmed by comparing the sequences of the genomic DNA and cDNA. It was revealed that no intron was present in the translation region.

Example 12

Expression of Saponin-Decomposing Enzyme Derived from *Eupenicillium brefeldianum* PF1226 (SDE) in *Trichoderma viride*

12a) Construction of Vector for Transformation

PCR was carried out with primers for *Trichoderma* secretion shown below using pSDEXho/IIKS+1 obtained in Example 11 as a template, as described in Example 4.

Figure 7:
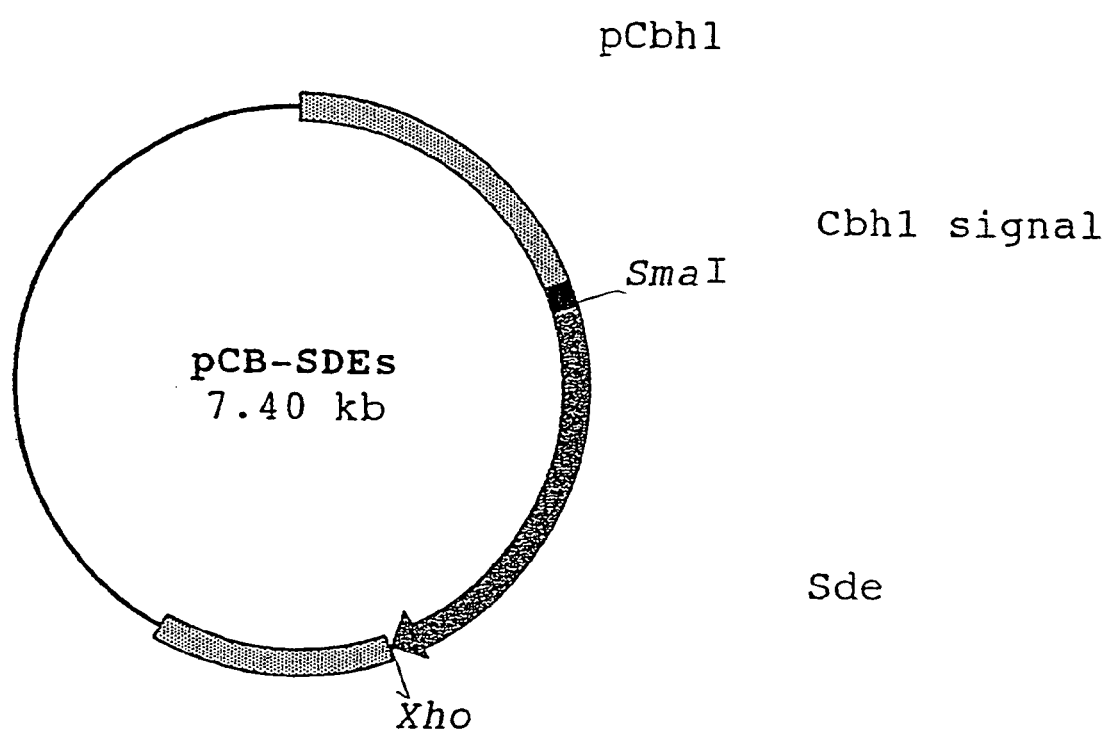
FIG. 7 shows the construction and restriction map for plasmid pCB-SDEs.

A fragment obtained by digesting the resultant PCR product with restriction enzymes SmaI and XhoI was ligated to plasmid pCB1-M2 (see Example 5 of WO 98/11239) previously digested with SmaI and XhoI, using a DNA ligation kit ver. 2 (Takara Shuzo Co., Ltd) to construct pCB-SDEs (FIG. 7).

```
N-terminal primer for SDE secretion in
Trichoderma:
                                    (SEQ ID NO: 51)
GGGCCCGGGCTCAGACTACCCCGGCACCTCCTCAGCC C-terminal primer for SDE secretion in
Trichoderma:
                                    (SEQ ID NO: 52)
GGGCTCGACTACCTCATGCACCATTGAGCGGCTGGTGG
```

12b) Transformation of *Trichoderma viride* and Detection of Saponin-Decomposing Activity of Each Recombinant Host cells of the uracyl-requiring *Trichoderma viride* strain obtained in 5b) of Example 5 were transformed by the co-transformation method using pCB-SDEs and vector pPYR4 in which the pyr4 cassette was linked to pLITMUS28 (see 5a) above), as described in 5c) in Example 5. As a result, about 28 strains of transformants per 1 μg of DNA were obtained.

Each of the transformants thus obtained was cultured (see Example 1 of WO 98/11239) and the resultant culture supernatant was subjected to SDS-PAGE, on which a band with an estimated molecular weight of about 67 kDa was observed only for the transformants.

Saponin-decomposing activity was measured as described in Test Example 1 for this culture supernatant. As a result, a spot of the decomposed product, soyasapogenol B, was observed on TLC.

12c) Purification of Recombinant Saponin-Decomposing Enzyme Derived from *Eupenicillium brefeldianum* PF 1226 (Recombinant SDE), and Comparison of Its Activity with the Wild-Type Saponin-Decomposing Enzyme Derived from *Eupenicillium brefeldianum* PF1226 (Wild-Type SDE)

The culture obtained in 12b) in Example 12 (about 900 ml) was centrifuged (8,000 rpm, 30 minutes) to remove cell debris. Ammonium sulfate (78.7 g) was added to about 690 ml of the supernatant thus obtained and the resulting precipitate was removed by centrifugation. Further, 88.6 g of ammonium sulfate (40% saturation fraction) were added to the resultant supernatant and the resultant precipitate was dissolved to make 120 ml of 1 M ammonium sulfate-0.1 M sodium phosphate buffer (pH 5.8). A 20 ml portion of this solution was subjected to hydrophobic chromatography using Butyl Toyopearl 650S, (26 mm i.d.×330 mm) (Tosoh Co.). Elution was carried out with a concentration gradient from a buffer solution A to a 0.1 M sodium phosphate buffer solution and a fraction eluted at an ammonium sulfate concentration from 0.2 M to 0 M was recovered.

The fraction thus obtained was concentrated using Pellicon XL (cut-off molecular weight: 10,000) (Millipore) and Ultrafree 15 (cut-off molecular weight: 5,000) (Millipore), desalted using a PD-10 column (Amersham Bioscience) and then subjected to ion-exchange chromatography using 6 ml of Resource Q (Amersham Bioscience) Elution was carried out with a concentration gradient from 50 mM Tris-HCl buffer (pH 7.5) to 50 mM Tris-HCl buffer-0.5 M sodium chloride (pH 7.5), and a fraction eluted at a salt concentration from 0 M to 0.1 M was recovered.

The fraction thus obtained was concentrated using Ultrafree 15 (cut-off molecular weight: 5,000) (Millipore) and then subjected to gel filtration chromatography using Superdex 200 pg (16 mm i.d.×600 mm) (Amersham Bioscience). Elution was carried out with a buffer solution G and a fraction of a cut-off molecular weight of about 50 kDa was recovered.

SDS-PAGE was carried out with this fraction and a single band with an estimated molecular weight of about 67 kDa was observed. Further, the cut-off molecular weight on the gel filtration and the molecular weight on the SDS-PAGE were different probably because this protein was adsorbed unspecifically to the carriers.

The optimum pH and the optimum temperature for the recombinant SDE thus purified and the saponin-decomposing enzyme purified in Example 9 (wild-type SDE) were measured according to Test Example 2.

The optimum pH and the optimum temperature were measured as described in 5d) in Example 5.

Figure 8:
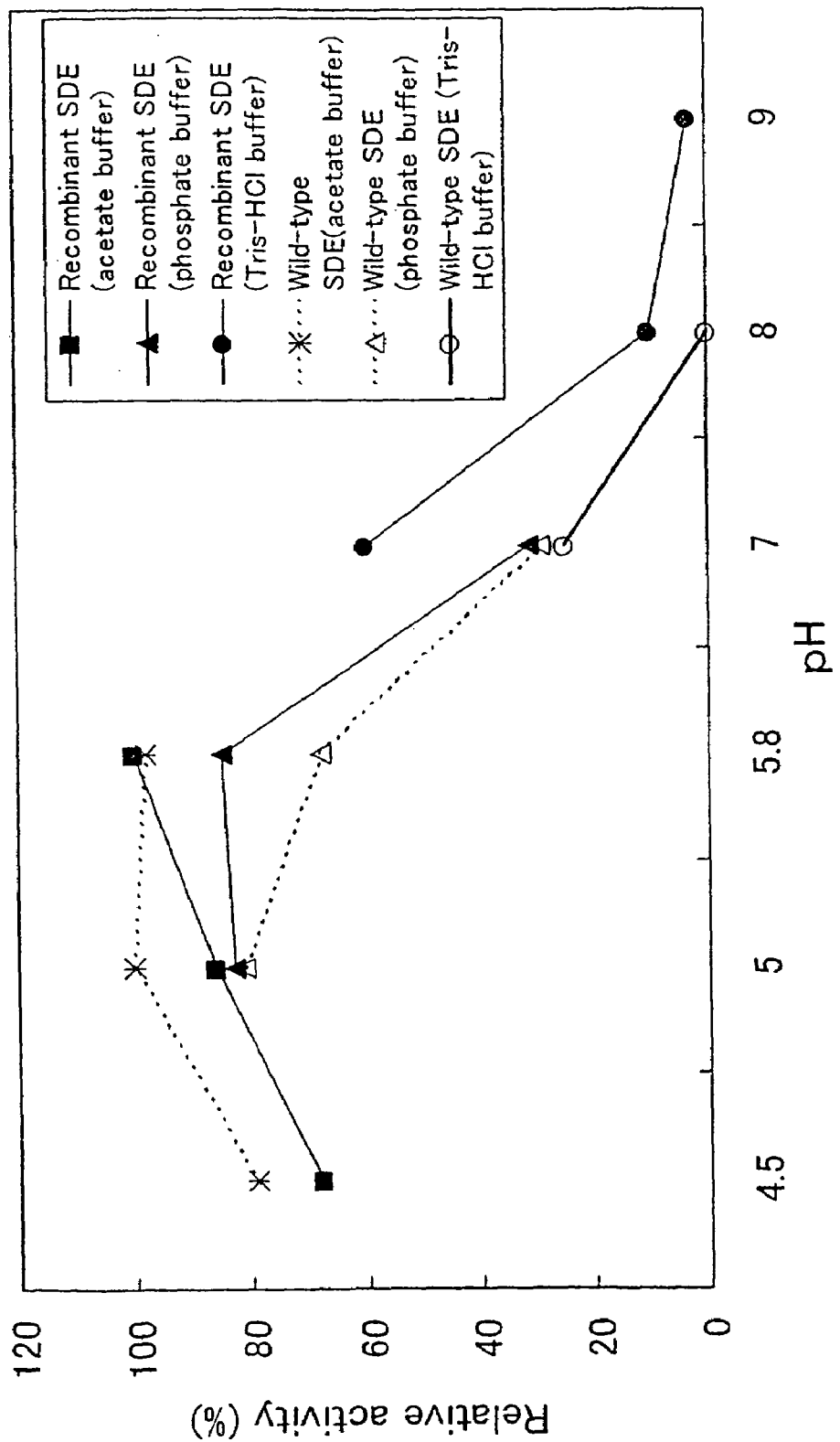
FIG. 8 shows the optimum pH for recombinant saponin-decomposing enzymes in Example 12. In the Figure, the wild-type SDE means the saponin-decomposing enzyme derived from *Eupenicillium brefeldianum* PF1226, and the recombinant SDN means the recombinant saponin-decomposing enzyme.
Figure 9:
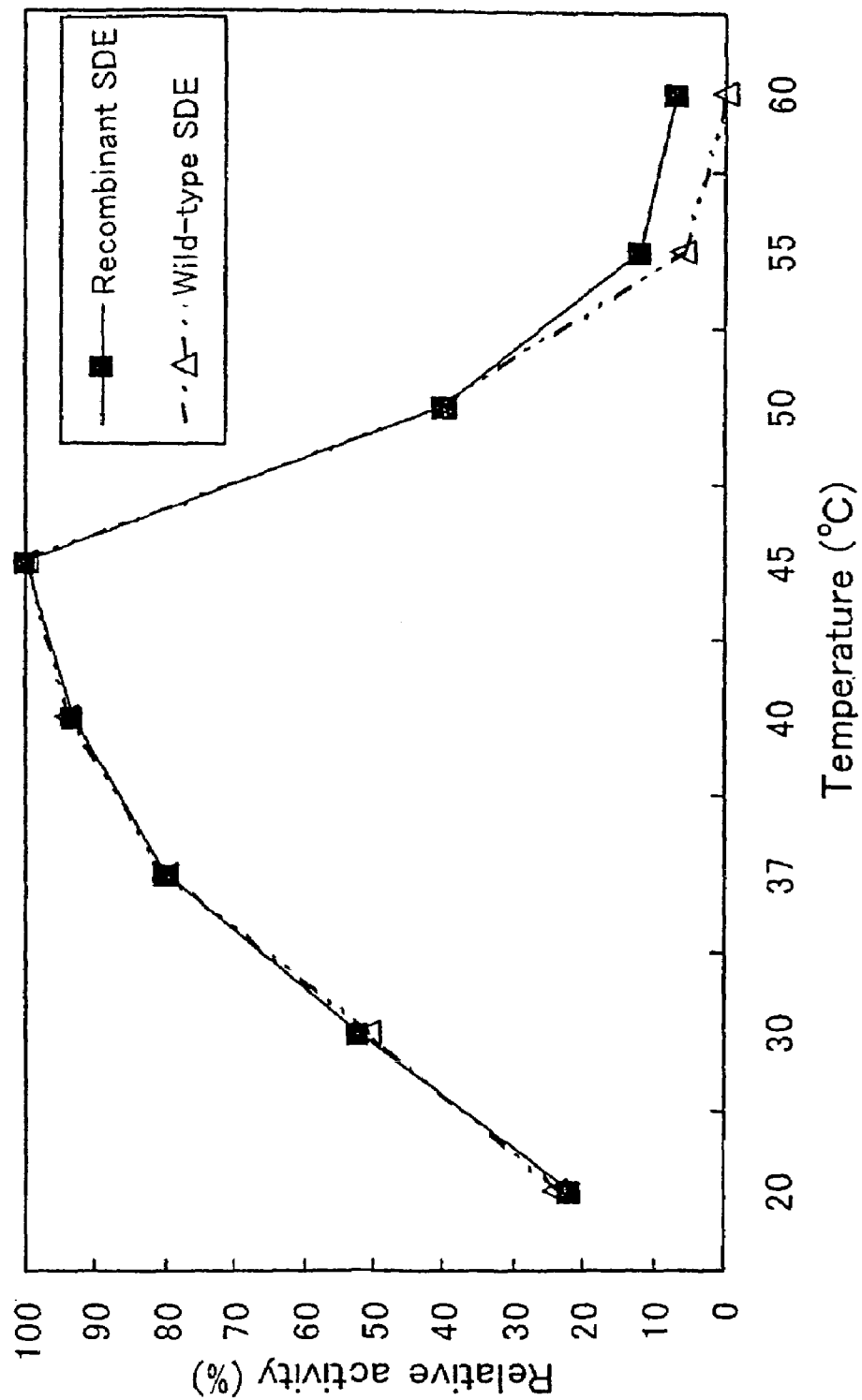
FIG. 9 shows the optimum temperature for recombinant saponin-decomposing enzymes in Example 12. In the Figure, the wild-type SDE means the saponin-decomposing enzyme derived from *Eupenicillium brefeldianum* PF1226, and the recombinant SDE means the recombinant saponin-decomposing enzyme.

Results are shown in FIGS. 8 and 9.

As a result, it was revealed that the recombinant SDE exhibited improved activity in a Tris-HCl buffer solution and also at high pHs as compared to the wild-type SDE.

The invention claimed is:

1. An isolated protein selected from the group consisting of:
   (a) a protein comprising the amino acid sequence of SEQ ID NO: 2; and
   (b) a protein that has at least 95% homology to the protein comprising the amino acid sequence of SEQ ID NO: 2 and having saponin-decomposing activity.

2. The isolated protein according to claim 1, which is encoded by a polynucleotide selected from the group consisting of:
   (i) a polynucleotide consisting of the DNA sequence of SEQ ID NO: 1;
   (ii) a polynucleotide that has at least 95% homology to the polynucleotide consisting of the DNA sequence of (i) and encodes a protein having saponin-decomposing activity; and
   (iii) a polynucleotide that hybridizes with a DNA sequence of a polynucleotide comprising the DNA sequence of (i) under stringent conditions and encodes a protein having saponin-decomposing activity wherein stringent conditions comprises a wash at 42° C. in 0.5×SSC, 0.4% SDS and 6M urea.

3. A method for producing soyasapogenol B, which comprises decomposing a glycoside having soyasapogenol B as an aglycone using the protein of claim 1.

* * * * *

SEQUENCE LISTING

```
<160> NUMBER OF SEQ ID NOS: 54

<210> SEQ ID NO 1
<211> LENGTH: 1917
<212> TYPE: DNA
<213> ORGANISM: Neocosmospora vasinfecta variety vasinfecta P1225
<220> FEATURE:
<221> NAME/KEY: CDS
<222> LOCATION: (1)..(1914)
<220> FEATURE:
<221> NAME/KEY: mat_peptide
<222> LOCATION: (79)..(1914)
<300> PUBLICATION INFORMATION:

<400> SEQUENCE: 1 atg cac ttc ttt gac aaa gcg act gtc tac gct ata ctc tgc ggt agc      48
Met His Phe Phe Asp Lys Ala Thr Val Tyr Ala Ile Leu Cys Gly Ser
    -25                 -20                 -15 gtg gcc cag act gtt cac gct gca ccc tcc gct tct cct cct gct tct      96
Val Ala Gln Thr Val His Ala Ala Pro Ser Ala Ser Pro Pro Ala Ser
-10                  -5                  -1   1                   5 gtt cca aac cct cct tct cct gag ccc att acc ctc aag cag cta cct     144
Val Pro Asn Pro Pro Ser Pro Glu Pro Ile Thr Leu Lys Gln Leu Pro
                 10                  15                  20 ctt cct ccc atc tcc cct agc gac gac gtc ggt gct tgc acg aag cag     192
Leu Pro Pro Ile Ser Pro Ser Asp Asp Val Gly Ala Cys Thr Lys Gln
             25                  30                  35 atc aac tct cgt gga acg gga tgt ctc gcc aac ggc gtt ttt gaa acg     240
Ile Asn Ser Arg Gly Thr Gly Cys Leu Ala Asn Gly Val Phe Glu Thr
         40                  45                  50 ttt cag tct ggt gac ttt tta cct gat gga aag cat gtc atc gcc atg     288
Phe Gln Ser Gly Asp Phe Leu Pro Asp Gly Lys His Val Ile Ala Met
 55                  60                  65                  70 gtc aac ttt act ggt gcg cct gct gct ccg gct gcg gga agc atc tac     336
Val Asn Phe Thr Gly Ala Pro Ala Ala Pro Ala Ala Gly Ser Ile Tyr
                 75                  80                  85 tct ggc ccg cag gtc atc atc gtc aag acg gat ggc aag aca ttt cct     384
Ser Gly Pro Gln Val Ile Ile Val Lys Thr Asp Gly Lys Thr Phe Pro
             90                  95                 100 aac gga gac ccc tgg aag tgc atc acc tgt ggt gtc cct gag aag aac     432
Asn Gly Asp Pro Trp Lys Cys Ile Thr Cys Gly Val Pro Glu Lys Asn
        105                 110                 115 gcc gtt ggt atc agc gtc aag tat gac tac ccc cag gcc ttt aag gat     480
Ala Val Gly Ile Ser Val Lys Tyr Asp Tyr Pro Gln Ala Phe Lys Asp
    120                 125                 130 ggc aaa cgt ctt ctc atc gga cac aat att ctc gac tgc ggc acc aac     528
Gly Lys Arg Leu Leu Ile Gly His Asn Ile Leu Asp Cys Gly Thr Asn
135                 140                 145                 150 cag ttg acg agc gag agc tgc aag cca gat aac acc cac atc tac cct     576
Gln Leu Thr Ser Glu Ser Cys Lys Pro Asp Asn Thr His Ile Tyr Pro
                155                 160                 165 atc cgc tgg aat gtt gct gcc gac ggt tcc ggc ccg agc ggt gaa atc     624
```

```
                                                    -continued

Ile Arg Trp Asn Val Ala Ala Asp Gly Ser Gly Pro Ser Gly Glu Ile
            170                 175                 180 cgt gag ctg cgg tta cac ccg gac aat gtc cat ctc gag ttt agc tct      672
Arg Glu Leu Arg Leu His Pro Asp Asn Val His Leu Glu Phe Ser Ser
            185                 190                 195 ttc acc ttt gct agt ggc agt att gga cag tat gcc tac ttt tct cgg      720
Phe Thr Phe Ala Ser Gly Ser Ile Gly Gln Tyr Ala Tyr Phe Ser Arg
            200                 205                 210 ctc gtt ttc aat cct tcg ccc aag act gga act ccc ctt gcg ccg cgg      768
Leu Val Phe Asn Pro Ser Pro Lys Thr Gly Thr Pro Leu Ala Pro Arg
215                 220                 225                 230 tat gac ctg gaa aag gtt act att ctg cac aac ccc gag ggc gtt gcc      816
Tyr Asp Leu Glu Lys Val Thr Ile Leu His Asn Pro Glu Gly Val Ala
            235                 240                 245 cct atc acg gcc aag ggt aag gtt ctg tct ctg aac ccc cag gct att      864
Pro Ile Thr Ala Lys Gly Lys Val Leu Ser Leu Asn Pro Gln Ala Ile
            250                 255                 260 tcg gtt ggc gag gct cgt ggc ttc aac ggc gac gga act gag ctc act      912
Ser Val Gly Glu Ala Arg Gly Phe Asn Gly Asp Gly Thr Glu Leu Thr
            265                 270                 275 tat gtc gga agc aat att gag agc tgt aat aat gat gtc ttt gcc gtt      960
Tyr Val Gly Ser Asn Ile Glu Ser Cys Asn Asn Asp Val Phe Ala Val
280                 285                 290 cat ctt caa act gga gtt gtt cga cgt ctt acc aac cat ccc gag tat     1008
His Leu Gln Thr Gly Val Val Arg Arg Leu Thr Asn His Pro Glu Tyr
295                 300                 305                 310 cct gac cct ctg gct ttc tcg cct gat aac aaa tgg atg gct gtc atg     1056
Pro Asp Pro Leu Ala Phe Ser Pro Asp Asn Lys Trp Met Ala Val Met
            315                 320                 325 gat acc cgc gga agt ggt cgc aac atg ttt att gcc ggc atg cga gga     1104
Asp Thr Arg Gly Ser Gly Arg Asn Met Phe Ile Ala Gly Met Arg Gly
            330                 335                 340 atc ccg ccc ctg gtt gat att gtt ggc ggt att ctg cca gcg tcg tct     1152
Ile Pro Pro Leu Val Asp Ile Val Gly Gly Ile Leu Pro Ala Ser Ser
            345                 350                 355 cgc aac aac ggt ctt cgt cgc ttc ttc cag ccg tac ctg ctt gat ttt     1200
Arg Asn Asn Gly Leu Arg Arg Phe Phe Gln Pro Tyr Leu Leu Asp Phe
            360                 365                 370 tat ggt gac cgc ggt gac tac tac ggc caa aag atc aac gga gat aac     1248
Tyr Gly Asp Arg Gly Asp Tyr Tyr Gly Gln Lys Ile Asn Gly Asp Asn
375                 380                 385                 390 aat ggc gtg cct ggg agt ggt gcc atc aac gat cct gag tgg aac ggt     1296
Asn Gly Val Pro Gly Ser Gly Ala Ile Asn Asp Pro Glu Trp Asn Gly
            395                 400                 405 atg gct gat ccg aga tgg tct cct gac agc agg cag ctc gtc ttt tgg     1344
Met Ala Asp Pro Arg Trp Ser Pro Asp Ser Arg Gln Leu Val Phe Trp
            410                 415                 420 cag act cat acc gtc tcc cct tct tgt ggc ggc gcc aac cct ctc cct     1392
Gln Thr His Thr Val Ser Pro Ser Cys Gly Gly Ala Asn Pro Leu Pro
            425                 430                 435 tgc tac cct tcg aaa gag caa ggt ggc cgt aac tat cgc atg tac atc     1440
Cys Tyr Pro Ser Lys Glu Gln Gly Gly Arg Asn Tyr Arg Met Tyr Ile
            440                 445                 450 gcg acc ttt act agc cgc agc cca agc cct cct gcc ccg gtg aag gag     1488
Ala Thr Phe Thr Ser Arg Ser Pro Ser Pro Pro Ala Pro Val Lys Glu
455                 460                 465                 470 cac tcc gat acc atc ccc tgg ggc gtc ccg tac gtt ccc gga tct cag     1536
His Ser Asp Thr Ile Pro Trp Gly Val Pro Tyr Val Pro Gly Ser Gln
            475                 480                 485
```

-continued

| | | | | | | | | | | | | | | | |
|---|---|---|---|---|---|---|---|---|---|---|---|---|---|---|---|
| gtt | act | cca | aag | cct | ggc | ttg | gcg | ggc | ggt | atc | tac | acg | ctc | tac | ggc | 1584 |
| Val | Thr | Pro | Lys | Pro | Gly | Leu | Ala | Gly | Gly | Ile | Tyr | Thr | Leu | Tyr | Gly |
| | | | 490 | | | | | 495 | | | | | 500 | | | aag gct tcg ggc gag gcc aag gtc aac atc acc tgg ggt gag gca ccc     1632
Lys Ala Ser Gly Glu Ala Lys Val Asn Ile Thr Trp Gly Glu Ala Pro
            505                 510                 515 gag att gga acc gtc agc gtc gtg tac aag gac tat tcg ctc gac ggc     1680
Glu Ile Gly Thr Val Ser Val Val Tyr Lys Asp Tyr Ser Leu Asp Gly
520                 525                 530 aag agc ttc ctc aac ggg aac gag agc gtc acg ggg tct gtc gag aga     1728
Lys Ser Phe Leu Asn Gly Asn Glu Ser Val Thr Gly Ser Val Glu Arg
535                 540                 545                 550 ctg act gac tat tct ttt gac tgg tat tcg gat att cgc cag acg gga     1776
Leu Thr Asp Tyr Ser Phe Asp Trp Tyr Ser Asp Ile Arg Gln Thr Gly
            555                 560                 565 gct gtc aag gga acc aag aag acg agc cct ggt gga ttc cat gct aat     1824
Ala Val Lys Gly Thr Lys Lys Thr Ser Pro Gly Gly Phe His Ala Asn
            570                 575                 580 att gat gtc atg atc aac gac ctg act tca act ggt act ctt acc acg     1872
Ile Asp Val Met Ile Asn Asp Leu Thr Ser Thr Gly Thr Leu Thr Thr
585                 590                 595 act ctg gat ggt gtt gag tgg cgt agt cct cag agc ggc act taa        1917
Thr Leu Asp Gly Val Glu Trp Arg Ser Pro Gln Ser Gly Thr
600                 605                 610

<210> SEQ ID NO 2
<211> LENGTH: 638
<212> TYPE: PRT
<213> ORGANISM: Neocosmospora vasinfecta variety vasinfecta P1225

<400> SEQUENCE: 2

Met His Phe Phe Asp Lys Ala Thr Val Tyr Ala Ile Leu Cys Gly Ser
        -25                 -20                 -15

Val Ala Gln Thr Val His Ala Ala Pro Ser Ala Ser Pro Pro Ala Ser
-10                  -5                  -1   1                   5

Val Pro Asn Pro Pro Ser Pro Glu Pro Ile Thr Leu Lys Gln Leu Pro
                10                  15                  20

Leu Pro Pro Ile Ser Pro Ser Asp Asp Val Gly Ala Cys Thr Lys Gln
            25                  30                  35

Ile Asn Ser Arg Gly Thr Gly Cys Leu Ala Asn Gly Val Phe Glu Thr
        40                  45                  50

Phe Gln Ser Gly Asp Phe Leu Pro Asp Gly Lys His Val Ile Ala Met
55                  60                  65                  70

Val Asn Phe Thr Gly Ala Pro Ala Pro Ala Ala Gly Ser Ile Tyr
                75                  80                  85

Ser Gly Pro Gln Val Ile Ile Val Lys Thr Asp Gly Lys Thr Phe Pro
            90                  95                  100

Asn Gly Asp Pro Trp Lys Cys Ile Thr Cys Gly Val Pro Glu Lys Asn
        105                 110                 115

Ala Val Gly Ile Ser Val Lys Tyr Asp Tyr Pro Gln Ala Phe Lys Asp
    120                 125                 130

Gly Lys Arg Leu Leu Ile Gly His Asn Ile Leu Asp Cys Gly Thr Asn
135                 140                 145                 150

Gln Leu Thr Ser Glu Ser Cys Lys Pro Asp Asn Thr His Ile Tyr Pro
                155                 160                 165

Ile Arg Trp Asn Val Ala Ala Asp Gly Ser Gly Pro Ser Gly Glu Ile
        170                 175                 180

-continued

```
Arg Glu Leu Arg Leu His Pro Asp Asn Val His Leu Glu Phe Ser Ser
            185                 190                 195

Phe Thr Phe Ala Ser Gly Ser Ile Gly Gln Tyr Ala Tyr Phe Ser Arg
    200                 205                 210

Leu Val Phe Asn Pro Ser Pro Lys Thr Gly Thr Pro Leu Ala Pro Arg
215                 220                 225                 230

Tyr Asp Leu Glu Lys Val Thr Ile Leu His Asn Pro Glu Gly Val Ala
                235                 240                 245

Pro Ile Thr Ala Lys Gly Lys Val Leu Ser Leu Asn Pro Gln Ala Ile
            250                 255                 260

Ser Val Gly Glu Ala Arg Gly Phe Asn Gly Asp Gly Thr Glu Leu Thr
            265                 270                 275

Tyr Val Gly Ser Asn Ile Glu Ser Cys Asn Asn Asp Val Phe Ala Val
            280                 285                 290

His Leu Gln Thr Gly Val Val Arg Arg Leu Thr Asn His Pro Glu Tyr
295                 300                 305                 310

Pro Asp Pro Leu Ala Phe Ser Pro Asp Asn Lys Trp Met Ala Val Met
                315                 320                 325

Asp Thr Arg Gly Ser Gly Arg Asn Met Phe Ile Ala Gly Met Arg Gly
            330                 335                 340

Ile Pro Pro Leu Val Asp Ile Val Gly Gly Ile Leu Pro Ala Ser Ser
            345                 350                 355

Arg Asn Asn Gly Leu Arg Arg Phe Gln Pro Tyr Leu Leu Asp Phe
            360                 365                 370

Tyr Gly Asp Arg Gly Asp Tyr Tyr Gly Gln Lys Ile Asn Gly Asp Asn
375                 380                 385                 390

Asn Gly Val Pro Gly Ser Gly Ala Ile Asn Asp Pro Glu Trp Asn Gly
                395                 400                 405

Met Ala Asp Pro Arg Trp Ser Pro Asp Ser Arg Gln Leu Val Phe Trp
                410                 415                 420

Gln Thr His Thr Val Ser Pro Ser Cys Gly Gly Ala Asn Pro Leu Pro
            425                 430                 435

Cys Tyr Pro Ser Lys Glu Gln Gly Gly Arg Asn Tyr Arg Met Tyr Ile
440                 445                 450

Ala Thr Phe Thr Ser Arg Ser Pro Ser Pro Ala Pro Val Lys Glu
455                 460                 465                 470

His Ser Asp Thr Ile Pro Trp Gly Val Pro Tyr Val Pro Gly Ser Gln
                475                 480                 485

Val Thr Pro Lys Pro Gly Leu Ala Gly Gly Ile Tyr Thr Leu Tyr Gly
            490                 495                 500

Lys Ala Ser Gly Glu Ala Lys Val Asn Ile Thr Trp Gly Glu Ala Pro
            505                 510                 515

Glu Ile Gly Thr Val Ser Val Val Tyr Lys Asp Tyr Ser Leu Asp Gly
            520                 525                 530

Lys Ser Phe Leu Asn Gly Asn Glu Ser Val Thr Gly Ser Val Glu Arg
535                 540                 545                 550

Leu Thr Asp Tyr Ser Phe Asp Trp Tyr Ser Asp Ile Arg Gln Thr Gly
                555                 560                 565

Ala Val Lys Gly Thr Lys Lys Thr Ser Pro Gly Gly Phe His Ala Asn
            570                 575                 580

Ile Asp Val Met Ile Asn Asp Leu Thr Ser Thr Gly Thr Leu Thr Thr
            585                 590                 595

Thr Leu Asp Gly Val Glu Trp Arg Ser Pro Gln Ser Gly Thr
```

-continued

```
<210> SEQ ID NO 3
<211> LENGTH: 1902
<212> TYPE: DNA
<213> ORGANISM: Aspergillus sp. PF1224
<220> FEATURE:
<221> NAME/KEY: CDS
<222> LOCATION: (1)..(1899)
<220> FEATURE:
<221> NAME/KEY: mat_peptide
<222> LOCATION: (85)..(1899)

<400> SEQUENCE: 3
```

| | | | | | | | | | | | | | | | | |
|---|---|---|---|---|---|---|---|---|---|---|---|---|---|---|---|---|
| atg | cat | gtt | gtc | gca | agt | acc | act | gct | ttt | ctg | ggc | gtc | gtt | tct | act | 48 |
| Met | His | Val | Val | Ala | Ser | Thr | Thr | Ala | Phe | Leu | Gly | Val | Val | Ser | Thr | |
| | | -25 | | | | -20 | | | | | -15 | | | | | |
| gtt | gct | ggg | gta | cac | cat | gtc | aac | aga | gac | acc | agt | caa | cag | atc | cta | 96 |
| Val | Ala | Gly | Val | His | His | Val | Asn | Arg | Asp | Thr | Ser | Gln | Gln | Ile | Leu | |
| | | -10 | | | | -5 | | | | -1 | 1 | | | | | |
| aaa | cca | cct | gta | cca | gag | cct | att | gtc | gtc | acc | gag | ctt | ccc | ttg | cct | 144 |
| Lys | Pro | Pro | Val | Pro | Glu | Pro | Ile | Val | Val | Thr | Glu | Leu | Pro | Leu | Pro | |
| 5 | | | | | 10 | | | | | 15 | | | | | 20 | |
| cct | gtc | gcc | gac | agt | aag | gag | ggc | tct | tgt | act | ccc | gaa | gtt | agc | cct | 192 |
| Pro | Val | Ala | Asp | Ser | Lys | Glu | Gly | Ser | Cys | Thr | Pro | Glu | Val | Ser | Pro | |
| | | | | 25 | | | | | 30 | | | | | 35 | | |
| cac | agg | acc | ggt | tgt | cta | ctc | aaa | tcc | tcc | cag | att | cag | agt | gga | aat | 240 |
| His | Arg | Thr | Gly | Cys | Leu | Leu | Lys | Ser | Ser | Gln | Ile | Gln | Ser | Gly | Asn | |
| | | | 40 | | | | | 45 | | | | | 50 | | | |
| ttc | ctt | cct | gac | aac | aat | cat | gtc | ctt | gtc | agc | tta | aac | ttc | tca | ggg | 288 |
| Phe | Leu | Pro | Asp | Asn | Asn | His | Val | Leu | Val | Ser | Leu | Asn | Phe | Ser | Gly | |
| | | 55 | | | | | 60 | | | | | 65 | | | | |
| gct | cca | gca | gct | cca | gat | ccg | gct | agc | att | tat | aat | ggt | acc | cat | ttg | 336 |
| Ala | Pro | Ala | Ala | Pro | Asp | Pro | Ala | Ser | Ile | Tyr | Asn | Gly | Thr | His | Leu | |
| | 70 | | | | | 75 | | | | | 80 | | | | | |
| act | ctg | ata | aag | gct | gat | ggg | acc | aac | ttt | cct | agt | ggt | gac | cca | tgg | 384 |
| Thr | Leu | Ile | Lys | Ala | Asp | Gly | Thr | Asn | Phe | Pro | Ser | Gly | Asp | Pro | Trp | |
| 85 | | | | | 90 | | | | | 95 | | | | | 100 | |
| aag | tgt | att | acc | tgc | ggc | gtg | ccg | gaa | gaa | aac | aag | gtc | ggc | agc | aca | 432 |
| Lys | Cys | Ile | Thr | Cys | Gly | Val | Pro | Glu | Glu | Asn | Lys | Val | Gly | Ser | Thr | |
| | | | | 105 | | | | | 110 | | | | | 115 | | |
| gaa | ctt | tcg | cca | tat | cct | cag | gcg | ttt | ttg | gat | ggc | aag | agg | gcc | tta | 480 |
| Glu | Leu | Ser | Pro | Tyr | Pro | Gln | Ala | Phe | Leu | Asp | Gly | Lys | Arg | Ala | Leu | |
| | | | 120 | | | | | 125 | | | | | 130 | | | |
| att | ggg | acc | aac | atc | gtt | gat | tgt | ggc | tcg | gcg | ctg | ctt | tca | agt | tca | 528 |
| Ile | Gly | Thr | Asn | Ile | Val | Asp | Cys | Gly | Ser | Ala | Leu | Leu | Ser | Ser | Ser | |
| | | 135 | | | | | 140 | | | | | 145 | | | | |
| gac | tgt | aca | ccg | gat | aaa | gtg | cat | atc | tac | cca | atc | cgc | tgg | aat | gtc | 576 |
| Asp | Cys | Thr | Pro | Asp | Lys | Val | His | Ile | Tyr | Pro | Ile | Arg | Trp | Asn | Val | |
| | 150 | | | | | 155 | | | | | 160 | | | | | |
| aag | gca | gat | ggc | tca | ggt | tcc | gga | ggg | aat | ata | cga | gaa | ttg | cgc | cta | 624 |
| Lys | Ala | Asp | Gly | Ser | Gly | Ser | Gly | Gly | Asn | Ile | Arg | Glu | Leu | Arg | Leu | |
| 165 | | | | | 170 | | | | | 175 | | | | | 180 | |
| cat | ccg | gac | aat | gtg | cac | tta | ggg | ttc | aac | tcc | ttc | acg | ttc | tct | aat | 672 |
| His | Pro | Asp | Asn | Val | His | Leu | Gly | Phe | Asn | Ser | Phe | Thr | Phe | Ser | Asn | |
| | | | | 185 | | | | | 190 | | | | | 195 | | |
| ggt | caa | cta | gga | cag | ttt | ggc | tac | ttt | agt | cga | ctg | cag | ttt | aac | cca | 720 |
| Gly | Gln | Leu | Gly | Gln | Phe | Gly | Tyr | Phe | Ser | Arg | Leu | Gln | Phe | Asn | Pro | |
| | | | 200 | | | | | 205 | | | | | 210 | | | |
| gcc | ccg | aag | act | ggc | gaa | cct | cgc | tca | gcc | cga | tat | gat | ctg | gtt | aac | 768 |
| Ala | Pro | Lys | Thr | Gly | Glu | Pro | Arg | Ser | Ala | Arg | Tyr | Asp | Leu | Val | Asn | |
| | | 215 | | | | | 220 | | | | | 225 | | | | |

| | |
|---|---|
| gtt acc aga ctc tat aac ccg gac agc cca cag cct atc agc gca aaa<br>Val Thr Arg Leu Tyr Asn Pro Asp Ser Pro Gln Pro Ile Ser Ala Lys<br>230                        235                        240 | 816 |
| ggc aac gag tta ttg ttt aac cga tcg gct att gcc gtc ggt gag ctt<br>Gly Asn Glu Leu Leu Phe Asn Arg Ser Ala Ile Ala Val Gly Glu Leu<br>245                        250                        255                        260 | 864 |
| cga gga ttt acc gga cgt ggc aaa gaa gtc aca tat atc ggc aac cct<br>Arg Gly Phe Thr Gly Arg Gly Lys Glu Val Thr Tyr Ile Gly Asn Pro<br>                        265                        270                        275 | 912 |
| gtc gag tca tgc aac atc gac gta ttc gct gcc gac ctg aca acc gga<br>Val Glu Ser Cys Asn Ile Asp Val Phe Ala Ala Asp Leu Thr Thr Gly<br>                        280                        285                        290 | 960 |
| aag gtc cgt cgg att aca gat cac ccc gag tat gtc gat ccg atg gat<br>Lys Val Arg Arg Ile Thr Asp His Pro Glu Tyr Val Asp Pro Met Asp<br>        295                        300                        305 | 1008 |
| gtc tct ccc gac gac aag tgg caa gtt atc ctc gat acc cga ggg acc<br>Val Ser Pro Asp Asp Lys Trp Gln Val Ile Leu Asp Thr Arg Gly Thr<br>310                        315                        320 | 1056 |
| ggt cga cag atg ttc atg gcc ggc atg cgc ggt att cca ccg atc atc<br>Gly Arg Gln Met Phe Met Ala Gly Met Arg Gly Ile Pro Pro Ile Ile<br>325                        330                        335                        340 | 1104 |
| gac ctg ata gct act acg gtc gca tcc tct act cgc aac aac ggc cct<br>Asp Leu Ile Ala Thr Thr Val Ala Ser Ser Thr Arg Asn Asn Gly Pro<br>                        345                        350                        355 | 1152 |
| cgg cga ttt ttc cga cct tgg ctc ctg gac cac gat ggg gac cgt gga<br>Arg Arg Phe Phe Arg Pro Trp Leu Leu Asp His Asp Gly Asp Arg Gly<br>                    360                        365                        370 | 1200 |
| gac tac tat ggc cag caa atc aac ggg gac ggt gac ggc agc ccg gga<br>Asp Tyr Tyr Gly Gln Gln Ile Asn Gly Asp Gly Asp Gly Ser Pro Gly<br>                375                        380                        385 | 1248 |
| agc atc aac gac cct aac tgg aac gcc ggg gca gat cca aag tgg tcc<br>Ser Ile Asn Asp Pro Asn Trp Asn Ala Gly Ala Asp Pro Lys Trp Ser<br>390                        395                        400 | 1296 |
| cac gac ggc acg cgc ata gca tac ttc gag aac ctg gtt gtt tct cct<br>His Asp Gly Thr Arg Ile Ala Tyr Phe Glu Asn Leu Val Val Ser Pro<br>405                        410                        415                        420 | 1344 |
| tct tgt ggc gga cag aac ccg ctg cct tgc cct aac tcc act gaa cca<br>Ser Cys Gly Gly Gln Asn Pro Leu Pro Cys Pro Asn Ser Thr Glu Pro<br>                        425                        430                        435 | 1392 |
| ggt ggt cgt gtc acc cgc ctg atg ctt gct cac ctg acc agc cgc gag<br>Gly Gly Arg Val Thr Arg Leu Met Leu Ala His Leu Thr Ser Arg Glu<br>                    440                        445                        450 | 1440 |
| ccg ctc gat ctt gaa ccc gtt gct cct gtc tct gat gaa gtt ccc tgg<br>Pro Leu Asp Leu Glu Pro Val Ala Pro Val Ser Asp Glu Val Pro Trp<br>                455                        460                        465 | 1488 |
| ggt gtt cca tac gtg ccc gag agt gct cta cca gac cgt ccc ttt cca<br>Gly Val Pro Tyr Val Pro Glu Ser Ala Leu Pro Asp Arg Pro Phe Pro<br>470                        475                        480 | 1536 |
| gct gaa gga aat tac acc ttg aag gga gag gtg tca ggc tca gct tct<br>Ala Glu Gly Asn Tyr Thr Leu Lys Gly Glu Val Ser Gly Ser Ala Ser<br>485                        490                        495                        500 | 1584 |
| gtg tca atc att cat gac aag acc att cca gca gcg atc aaa act atc<br>Val Ser Ile Ile His Asp Lys Thr Ile Pro Ala Ala Ile Lys Thr Ile<br>                        505                        510                        515 | 1632 |
| gca gtc acc tat cgc aac tat tcc gat gat ggg ttg cat gtt atc gca<br>Ala Val Thr Tyr Arg Asn Tyr Ser Asp Asp Gly Leu His Val Ile Ala<br>                    520                        525                        530 | 1680 |
| ggg tct gaa aga ttc acc aat act gtc gca tcc atg aca ata aac aag<br>Gly Ser Glu Arg Phe Thr Asn Thr Val Ala Ser Met Thr Ile Asn Lys | 1728 |

```
                    535                 540                 545
gtc gac tgg ttt tcc gac ctt acg tct acc gga caa gtg acc gga agc    1776
Val Asp Trp Phe Ser Asp Leu Thr Ser Thr Gly Gln Val Thr Gly Ser
550                 555                 560 aag aag acc agt ccc ggt ggg ttc cat ctg gag att gat gct atg act    1824
Lys Lys Thr Ser Pro Gly Gly Phe His Leu Glu Ile Asp Ala Met Thr
565                 570                 575                 580 aac atc ttc atg gca aac gga acc ttg aca acc act atc gat gga aag    1872
Asn Ile Phe Met Ala Asn Gly Thr Leu Thr Thr Thr Ile Asp Gly Lys
                585                 590                 595 gtc tgg aag cag ccg gca aat ggg act tga                            1902
Val Trp Lys Gln Pro Ala Asn Gly Thr
600                 605
```

<210> SEQ ID NO 4
<211> LENGTH: 633
<212> TYPE: PRT
<213> ORGANISM: Aspergillus sp. PF1224

<400> SEQUENCE: 4

```
Met His Val Val Ala Ser Thr Thr Ala Phe Leu Gly Val Val Ser Thr
            -25                 -20                 -15

Val Ala Gly Val His His Val Asn Arg Asp Thr Ser Gln Gln Ile Leu
        -10                  -5                  -1   1

Lys Pro Pro Val Pro Glu Pro Ile Val Val Thr Glu Leu Pro Leu Pro
  5                  10                  15                  20

Pro Val Ala Asp Ser Lys Glu Gly Ser Cys Thr Pro Glu Val Ser Pro
                25                  30                  35

His Arg Thr Gly Cys Leu Leu Lys Ser Ser Gln Ile Gln Ser Gly Asn
            40                  45                  50

Phe Leu Pro Asp Asn Asn His Val Leu Val Ser Leu Asn Phe Ser Gly
        55                  60                  65

Ala Pro Ala Ala Pro Asp Pro Ala Ser Ile Tyr Asn Gly Thr His Leu
    70                  75                  80

Thr Leu Ile Lys Ala Asp Gly Thr Asn Phe Pro Ser Gly Asp Pro Trp
 85                  90                  95                 100

Lys Cys Ile Thr Cys Gly Val Pro Glu Glu Asn Lys Val Gly Ser Thr
                105                 110                 115

Glu Leu Ser Pro Tyr Pro Gln Ala Phe Leu Asp Gly Lys Arg Ala Leu
            120                 125                 130

Ile Gly Thr Asn Ile Val Asp Cys Gly Ser Ala Leu Leu Ser Ser Ser
        135                 140                 145

Asp Cys Thr Pro Asp Lys Val His Ile Tyr Pro Ile Arg Trp Asn Val
    150                 155                 160

Lys Ala Asp Gly Ser Gly Ser Gly Asn Ile Arg Glu Leu Arg Leu
165                 170                 175                 180

His Pro Asp Asn Val His Leu Gly Phe Asn Ser Phe Thr Phe Ser Asn
                185                 190                 195

Gly Gln Leu Gly Gln Phe Gly Tyr Phe Ser Arg Leu Gln Phe Asn Pro
            200                 205                 210

Ala Pro Lys Thr Gly Glu Pro Arg Ser Ala Arg Tyr Asp Leu Val Asn
        215                 220                 225

Val Thr Arg Leu Tyr Asn Pro Asp Ser Pro Gln Pro Ile Ser Ala Lys
    230                 235                 240

Gly Asn Glu Leu Leu Phe Asn Arg Ser Ala Ile Ala Val Gly Glu Leu
245                 250                 255                 260
```

Arg Gly Phe Thr Gly Arg Gly Lys Glu Val Thr Tyr Ile Gly Asn Pro
              265                 270                 275

Val Glu Ser Cys Asn Ile Asp Val Phe Ala Asp Leu Thr Thr Gly
          280                 285                 290

Lys Val Arg Arg Ile Thr Asp His Pro Glu Tyr Val Asp Pro Met Asp
          295                 300                 305

Val Ser Pro Asp Lys Trp Gln Val Ile Leu Asp Thr Arg Gly Thr
      310                 315                 320

Gly Arg Gln Met Phe Met Ala Gly Met Arg Gly Ile Pro Pro Ile Ile
325                 330                 335                 340

Asp Leu Ile Ala Thr Thr Val Ala Ser Ser Thr Arg Asn Asn Gly Pro
              345                 350                 355

Arg Arg Phe Phe Arg Pro Trp Leu Leu Asp His Asp Gly Asp Arg Gly
              360                 365                 370

Asp Tyr Tyr Gly Gln Gln Ile Asn Gly Asp Gly Ser Pro Gly
      375                 380                 385

Ser Ile Asn Asp Pro Asn Trp Asn Ala Gly Ala Asp Pro Lys Trp Ser
      390                 395                 400

His Asp Gly Thr Arg Ile Ala Tyr Phe Glu Asn Leu Val Val Ser Pro
405                 410                 415                 420

Ser Cys Gly Gly Gln Asn Pro Leu Pro Cys Pro Asn Ser Thr Glu Pro
              425                 430                 435

Gly Gly Arg Val Thr Arg Leu Met Leu Ala His Leu Thr Ser Arg Glu
              440                 445                 450

Pro Leu Asp Leu Glu Pro Val Ala Pro Val Ser Asp Glu Val Pro Trp
      455                 460                 465

Gly Val Pro Tyr Val Pro Glu Ser Ala Leu Pro Asp Arg Pro Phe Pro
      470                 475                 480

Ala Glu Gly Asn Tyr Thr Leu Lys Gly Glu Val Ser Gly Ser Ala Ser
485                 490                 495                 500

Val Ser Ile Ile His Asp Lys Thr Ile Pro Ala Ala Ile Lys Thr Ile
              505                 510                 515

Ala Val Thr Tyr Arg Asn Tyr Ser Asp Asp Gly Leu His Val Ile Ala
              520                 525                 530

Gly Ser Glu Arg Phe Thr Asn Thr Val Ala Ser Met Thr Ile Asn Lys
              535                 540                 545

Val Asp Trp Phe Ser Asp Leu Thr Ser Thr Gln Val Thr Gly Ser
      550                 555                 560

Lys Lys Thr Ser Pro Gly Gly Phe His Leu Glu Ile Asp Ala Met Thr
565                 570                 575                 580

Asn Ile Phe Met Ala Asn Gly Thr Leu Thr Thr Ile Asp Gly Lys
              585                 590                 595

Val Trp Lys Gln Pro Ala Asn Gly Thr
              600                 605

<210> SEQ ID NO 5
<211> LENGTH: 1857
<212> TYPE: DNA
<213> ORGANISM: Eupenicillium brefeldianum PF1226
<220> FEATURE:
<221> NAME/KEY: CDS
<222> LOCATION: (1)..(1854)
<220> FEATURE:
<221> NAME/KEY: mat_peptide
<222> LOCATION: (52)..(1854)

<400> SEQUENCE: 5

```
atg cgt tgg agt ttc tct gtt gtc cta agc acg gct gcc ctt ggt ata      48
Met Arg Trp Ser Phe Ser Val Val Leu Ser Thr Ala Ala Leu Gly Ile
    -15              -10                  -5 tcc tcg act acc ccg gca cct cct cag cca gag ccc att gaa gta gtt      96
Ser Ser Thr Thr Pro Ala Pro Pro Gln Pro Glu Pro Ile Glu Val Val
 -1   1               5                  10                  15 gaa ctt ccc cta cct ccg gtt gca cca agc aac agt acg ggc gca tgc     144
Glu Leu Pro Leu Pro Pro Val Ala Pro Ser Asn Ser Thr Gly Ala Cys
                 20                  25                  30 acg gca tcc atc aac ccc cac cgg aca ggc tgc att gcg cag gta tca     192
Thr Ala Ser Ile Asn Pro His Arg Thr Gly Cys Ile Ala Gln Val Ser
             35                  40                  45 gac tct ttc cag gct ggc gac ttt aca cct gat gga aac cat gtg gtc     240
Asp Ser Phe Gln Ala Gly Asp Phe Thr Pro Asp Gly Asn His Val Val
         50                  55                  60 atc acc gtg gag ttt gtt ggt gct ccg gcg gca cca gac cca gcc agc     288
Ile Thr Val Glu Phe Val Gly Ala Pro Ala Ala Pro Asp Pro Ala Ser
     65                  70                  75 ata tac tct ggg gaa cat atc atc ctc gtc aaa gca gac ggt aca acg     336
Ile Tyr Ser Gly Glu His Ile Ile Leu Val Lys Ala Asp Gly Thr Thr
 80                  85                  90                  95 ttc acc aat ggc gat gca tgg aaa tgc tta agc tgc ggt gtt cct tcc     384
Phe Thr Asn Gly Asp Ala Trp Lys Cys Leu Ser Cys Gly Val Pro Ser
                100                 105                 110 aaa aat gcc ctt agc ctc gac ccg cag aga gac tat cca cat gtg gct     432
Lys Asn Ala Leu Ser Leu Asp Pro Gln Arg Asp Tyr Pro His Val Ala
                115                 120                 125 aga aat tct cga caa gcc ctt tgg gga cac aat atc ctg gat tgc agt     480
Arg Asn Ser Arg Gln Ala Leu Trp Gly His Asn Ile Leu Asp Cys Ser
            130                 135                 140 ggc att cct ctg gtc agc gat gag tgc acg cca aac aag acg cat atc     528
Gly Ile Pro Leu Val Ser Asp Glu Cys Thr Pro Asn Lys Thr His Ile
        145                 150                 155 tat cca atc tac tgg ccc acc ggc acg aac agc tcg ggc agc act cgg     576
Tyr Pro Ile Tyr Trp Pro Thr Gly Thr Asn Ser Ser Gly Ser Thr Arg
160                 165                 170                 175 gaa atg cgt ctg cat cct gac gat acg cac atg ggc tgg agc tca ttc     624
Glu Met Arg Leu His Pro Asp Asp Thr His Met Gly Trp Ser Ser Phe
                180                 185                 190 acc agt ggt ggt caa ttc gca tac ttt ggt cga ctg cag ttc cgt caa     672
Thr Ser Gly Gly Gln Phe Ala Tyr Phe Gly Arg Leu Gln Phe Arg Gln
                195                 200                 205 aat cca acc gac ggg aca ctt cgt gtt cca aga tat gat ctc gtc gat     720
Asn Pro Thr Asp Gly Thr Leu Arg Val Pro Arg Tyr Asp Leu Val Asp
            210                 215                 220 gtc aat ctg ctc gtc cag ccc aat ggt act gcg cct atc atg gcc cag     768
Val Asn Leu Leu Val Gln Pro Asn Gly Thr Ala Pro Ile Met Ala Gln
        225                 230                 235 ggc tct gaa ctg aag atc cat aat gaa gct att aca gtt ggt gag ctt     816
Gly Ser Glu Leu Lys Ile His Asn Glu Ala Ile Thr Val Gly Glu Leu
240                 245                 250                 255 cgc gga ttc agc ggc gcc gga gac gag atc ctg tac att ggg tcg aca     864
Arg Gly Phe Ser Gly Ala Gly Asp Glu Ile Leu Tyr Ile Gly Ser Thr
                260                 265                 270 cgt gag gca aac aac att gat ctc ttt gcg gtc cat atc act act ggc     912
Arg Glu Ala Asn Asn Ile Asp Leu Phe Ala Val His Ile Thr Thr Gly
                275                 280                 285 gct gtt cgc cgt ctc acc agt cac cct gag tac gct gat ccc att gcc     960
```

-continued

```
                Ala Val Arg Arg Leu Thr Ser His Pro Glu Tyr Ala Asp Pro Ile Ala
                        290                 295                 300 ttt tca cat gac aac caa tgg ttc gtc acc atg gac act cgt ggc tca      1008
Phe Ser His Asp Asn Gln Trp Phe Val Thr Met Asp Thr Arg Gly Ser
305                 310                 315 aat cga cag atg tgg atg gct ggg gag cgg tat att cct cct ctg att      1056
Asn Arg Gln Met Trp Met Ala Gly Glu Arg Tyr Ile Pro Pro Leu Ile
320                 325                 330                 335 gac ctg gtc act gtc aca gct gct tca tca act cgc aat aac ggc gcg      1104
Asp Leu Val Thr Val Thr Ala Ala Ser Ser Thr Arg Asn Asn Gly Ala
                340                 345                 350 cgc cgc ttc ttt cag cca atc ctg atc gat cgt tac ggt gat cgg gga      1152
Arg Arg Phe Phe Gln Pro Ile Leu Ile Asp Arg Tyr Gly Asp Arg Gly
                355                 360                 365 gac tac ttt ggt caa cga gtc aac tat caa ggc gac gga agc aat ggc      1200
Asp Tyr Phe Gly Gln Arg Val Asn Tyr Gln Gly Asp Gly Ser Asn Gly
            370                 375                 380 agt gtc aac gac ccg aat tgg aat ggc aga gca gac cca gcc ttc tct      1248
Ser Val Asn Asp Pro Asn Trp Asn Gly Arg Ala Asp Pro Ala Phe Ser
385                 390                 395 ccc gat gga act cgt atc gtc tat tgg cag gcc ttg gtg att cca cct      1296
Pro Asp Gly Thr Arg Ile Val Tyr Trp Gln Ala Leu Val Ile Pro Pro
400                 405                 410                 415 gcc tgc ggt ggt gca aat cca ctc ccc tgc cca gtg tca act gcc caa      1344
Ala Cys Gly Gly Ala Asn Pro Leu Pro Cys Pro Val Ser Thr Ala Gln
                420                 425                 430 gga ggt cga aca tac cga gtg atg ctg gca cgt ctt tca gat cgc aaa      1392
Gly Gly Arg Thr Tyr Arg Val Met Leu Ala Arg Leu Ser Asp Arg Lys
                435                 440                 445 cac acg gac cca gcc cct gtt ttt gct gcg cca gat tat att tct tgg      1440
His Thr Asp Pro Ala Pro Val Phe Ala Ala Pro Asp Tyr Ile Ser Trp
            450                 455                 460 gcg act ccg ttc cca cca ggt gca ggt ctt cct acg tct tat acc ctg      1488
Ala Thr Pro Phe Pro Pro Gly Ala Gly Leu Pro Thr Ser Tyr Thr Leu
465                 470                 475 cct gcg ggt aac tac act ctc tac ggc aag gct act ggg ctt gca aat      1536
Pro Ala Gly Asn Tyr Thr Leu Tyr Gly Lys Ala Thr Gly Leu Ala Asn
480                 485                 490                 495 gcc acc ctg acc agg gac cca ctt ttc ggc agc ttt aag act gta tcc      1584
Ala Thr Leu Thr Arg Asp Pro Leu Phe Gly Ser Phe Lys Thr Val Ser
                500                 505                 510 gtc aac tac acg aat ttc tca gat gat ggc cag cac ttt atc aat ggc      1632
Val Asn Tyr Thr Asn Phe Ser Asp Asp Gly Gln His Phe Ile Asn Gly
                515                 520                 525 tat gaa tct gtt act ctg acg ttg tct gcc tcg aac cct tgg ctt agc      1680
Tyr Glu Ser Val Thr Leu Thr Leu Ser Ala Ser Asn Pro Trp Leu Ser
            530                 535                 540 cat ttg gac tgg gtc tcc gat att gtg cag act ggt gct gtg aac gct      1728
His Leu Asp Trp Val Ser Asp Ile Val Gln Thr Gly Ala Val Asn Ala
545                 550                 555 gtt aag gag act ggg tct ggt gga ttt cat ttg aca atc gat gca cag      1776
Val Lys Glu Thr Gly Ser Gly Gly Phe His Leu Thr Ile Asp Ala Gln
560                 565                 570                 575 gag aac att ttt gag gct aat ggg aca ctg act acg act gtt gat ggc      1824
Glu Asn Ile Phe Glu Ala Asn Gly Thr Leu Thr Thr Thr Val Asp Gly
                580                 585                 590 gtg acc tac cac cag ccg ctc aat ggt gca tga                          1857
Val Thr Tyr His Gln Pro Leu Asn Gly Ala
            595                 600
```

<210> SEQ ID NO 6
<211> LENGTH: 618
<212> TYPE: PRT
<213> ORGANISM: Eupenicillium brefeldianum PF1226

<400> SEQUENCE: 6

```
Met Arg Trp Ser Phe Ser Val Val Leu Ser Thr Ala Ala Leu Gly Ile
        -15                 -10                  -5

Ser Ser Thr Thr Pro Ala Pro Pro Gln Pro Glu Pro Ile Glu Val Val
 -1   1               5                  10                  15

Glu Leu Pro Leu Pro Pro Val Ala Pro Ser Asn Ser Thr Gly Ala Cys
                 20                  25                  30

Thr Ala Ser Ile Asn Pro His Arg Thr Gly Cys Ile Ala Gln Val Ser
             35                  40                  45

Asp Ser Phe Gln Ala Gly Asp Phe Thr Pro Asp Gly Asn His Val Val
         50                  55                  60

Ile Thr Val Glu Phe Val Gly Ala Pro Ala Ala Pro Asp Pro Ala Ser
     65                  70                  75

Ile Tyr Ser Gly Glu His Ile Ile Leu Val Lys Ala Asp Gly Thr Thr
 80                  85                  90                  95

Phe Thr Asn Gly Asp Ala Trp Lys Cys Leu Ser Cys Gly Val Pro Ser
                100                 105                 110

Lys Asn Ala Leu Ser Leu Asp Pro Gln Arg Asp Tyr Pro His Val Ala
                115                 120                 125

Arg Asn Ser Arg Gln Ala Leu Trp Gly His Asn Ile Leu Asp Cys Ser
            130                 135                 140

Gly Ile Pro Leu Val Ser Asp Glu Cys Thr Pro Asn Lys Thr His Ile
        145                 150                 155

Tyr Pro Ile Tyr Trp Pro Thr Gly Thr Asn Ser Ser Gly Ser Thr Arg
160                 165                 170                 175

Glu Met Arg Leu His Pro Asp Asp Thr His Met Gly Trp Ser Ser Phe
                180                 185                 190

Thr Ser Gly Gly Gln Phe Ala Tyr Phe Gly Arg Leu Gln Phe Arg Gln
                195                 200                 205

Asn Pro Thr Asp Gly Thr Leu Arg Val Pro Arg Tyr Asp Leu Val Asp
            210                 215                 220

Val Asn Leu Leu Val Gln Pro Asn Gly Thr Ala Pro Ile Met Ala Gln
        225                 230                 235

Gly Ser Glu Leu Lys Ile His Asn Glu Ala Ile Thr Val Gly Glu Leu
240                 245                 250                 255

Arg Gly Phe Ser Gly Ala Gly Asp Glu Ile Leu Tyr Ile Gly Ser Thr
                260                 265                 270

Arg Glu Ala Asn Asn Ile Asp Leu Phe Ala Val His Ile Thr Thr Gly
            275                 280                 285

Ala Val Arg Arg Leu Thr Ser His Pro Glu Tyr Ala Asp Pro Ile Ala
        290                 295                 300

Phe Ser His Asp Asn Gln Trp Phe Val Thr Met Asp Thr Arg Gly Ser
305                 310                 315

Asn Arg Gln Met Trp Met Ala Gly Glu Arg Tyr Ile Pro Pro Leu Ile
320                 325                 330                 335

Asp Leu Val Thr Val Thr Ala Ala Ser Ser Thr Arg Asn Asn Gly Ala
                340                 345                 350

Arg Arg Phe Phe Gln Pro Ile Leu Ile Asp Arg Tyr Gly Asp Arg Gly
            355                 360                 365
```

-continued

```
Asp Tyr Phe Gly Gln Arg Val Asn Tyr Gln Gly Asp Gly Ser Asn Gly
        370                 375                 380

Ser Val Asn Asp Pro Asn Trp Asn Gly Arg Ala Asp Pro Ala Phe Ser
    385                 390                 395

Pro Asp Gly Thr Arg Ile Val Tyr Trp Gln Ala Leu Val Ile Pro Pro
400                 405                 410                 415

Ala Cys Gly Gly Ala Asn Pro Leu Pro Cys Pro Val Ser Thr Ala Gln
                420                 425                 430

Gly Gly Arg Thr Tyr Arg Val Met Leu Ala Arg Leu Ser Asp Arg Lys
            435                 440                 445

His Thr Asp Pro Ala Pro Val Phe Ala Ala Pro Asp Tyr Ile Ser Trp
        450                 455                 460

Ala Thr Pro Phe Pro Pro Gly Ala Gly Leu Pro Thr Ser Tyr Thr Leu
    465                 470                 475

Pro Ala Gly Asn Tyr Thr Leu Tyr Gly Lys Ala Thr Gly Leu Ala Asn
480                 485                 490                 495

Ala Thr Leu Thr Arg Asp Pro Leu Phe Gly Ser Phe Lys Thr Val Ser
                500                 505                 510

Val Asn Tyr Thr Asn Phe Ser Asp Asp Gly Gln His Phe Ile Asn Gly
            515                 520                 525

Tyr Glu Ser Val Thr Leu Thr Leu Ser Ala Ser Asn Pro Trp Leu Ser
        530                 535                 540

His Leu Asp Trp Val Ser Asp Ile Val Gln Thr Gly Ala Val Asn Ala
    545                 550                 555

Val Lys Glu Thr Gly Ser Gly Gly Phe His Leu Thr Ile Asp Ala Gln
560                 565                 570                 575

Glu Asn Ile Phe Glu Ala Asn Gly Thr Leu Thr Thr Thr Val Asp Gly
                580                 585                 590

Val Thr Tyr His Gln Pro Leu Asn Gly Ala
            595                 600

<210> SEQ ID NO 7
<211> LENGTH: 19
<212> TYPE: PRT
<213> ORGANISM: Neocosmospora vasinfecta variety vasinfecta P1225

<400> SEQUENCE: 7

Ala Ser Pro Pro Ala Ser Val Pro Asn Asn Pro Ser Ser Glu Glu Ile
  1               5                  10                  15

Thr Leu Gln

<210> SEQ ID NO 8
<211> LENGTH: 8
<212> TYPE: PRT
<213> ORGANISM: Neocosmospora vasinfecta variety vasinfecta P1225

<400> SEQUENCE: 8

Leu Val Phe Asn Pro Ser Pro Lys
  1               5

<210> SEQ ID NO 9
<211> LENGTH: 15
<212> TYPE: PRT
<213> ORGANISM: Neocosmospora vasinfecta variety vasinfecta P1225

<400> SEQUENCE: 9

Trp Asn Val Ala Ala Asp Gly Ser Gly Pro Ser Gly Glu Ile Arg
```

-continued

```
<210> SEQ ID NO 10
<211> LENGTH: 16
<212> TYPE: PRT
<213> ORGANISM: Neocosmospora vasinfecta variety vasinfecta P1225

<400> SEQUENCE: 10

Val Thr Ile Leu His Asn Pro Glu Gly Val Ala Pro Ile Thr Ala Lys
 1               5                  10                  15

<210> SEQ ID NO 11
<211> LENGTH: 17
<212> TYPE: PRT
<213> ORGANISM: Neocosmospora vasinfecta variety vasinfecta P1225

```
<221> NAME/KEY: modified_base
<222> LOCATION: (3)
<223> OTHER INFORMATION: n = a c g or t
<220> FEATURE:
<221> NAME/KEY: modified_base
<222> LOCATION: (6)
<223> OTHER INFORMATION: n = a c g or t
<220> FEATURE:
<221> NAME/KEY: modified_base
<222> LOCATION: (9)
<223> OTHER INFORMATION: y =  c or t
<220> FEATURE:
<221> NAME/KEY: modified_base
<222> LOCATION: (12)
<223> OTHER INFORMATION: n = a c g or t
<220> FEATURE:
<221> NAME/KEY: modified_base
<222> LOCATION: (15)
<223> OTHER INFORMATION: n = a c g or t

<400> SEQUENCE: 14
ccngcnagyg tnccnaa                                                      17

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: r = a or g
<220> FEATURE:
<221> NAME/KEY: modified_base
<222> LOCATION: (6)
<223> OTHER INFORMATION: n = a c g or t
<220> FEATURE:
<221> NAME/KEY: modified_base
<222> LOCATION: (9)
<223> OTHER INFORMATION: n = a c g or t
<220> FEATURE:
<221> NAME/KEY: modified_base
<222> LOCATION: (12)
<223> OTHER INFORMATION: n = a c g or t
<220> FEATURE:
<221> NAME/KEY: modified_base
<222> LOCATION: (15)
<223> OTHER INFORMATION: r = a or g

<400> SEQUENCE: 15
ccrtcngcng cnacrtt                                                      17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (6)
<223> OTHER INFORMATION: n = a c g or t
<220> FEATURE:
<221> NAME/KEY: modified_base
<222> LOCATION: (9)
<223> OTHER INFORMATION: d = a g or t
<220> FEATURE:
<221> NAME/KEY: modified_base
<222> LOCATION: (12)
<223> OTHER INFORMATION: n = a c g or t
<220> FEATURE:
<221> NAME/KEY: modified_base
```

```
<222> LOCATION: (15)
<223> OTHER INFORMATION: r = a or g

<400> SEQUENCE: 16
ccccanggda tngtrtc                                                    17

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: n = a c g or t
<220> FEATURE:
<221> NAME/KEY: modified_base
<222> LOCATION: (6)
<223> OTHER INFORMATION: y =  c or t
<220> FEATURE:
<221> NAME/KEY: modified_base
<222> LOCATION: (9)
<223> OTHER INFORMATION: n = a c g or t
<220> FEATURE:
<221> NAME/KEY: modified_base
<222> LOCATION: (12)
<223> OTHER INFORMATION: r = a or g
<220> FEATURE:
<221> NAME/KEY: modified_base
<222> LOCATION: (15)
<223> OTHER INFORMATION: r = a or g

<400> SEQUENCE: 17
acnccytcng grttrtg                                                    17

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 18
tgacgctgat accaacggcg                                                 20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 19
ctagtggcag tattggacag                                                 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 20
cccaggcctt taaggatggc                                                 20
```

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 21
ctgcttgagg gtaatgggct c                                            21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 22
acagacgccg gaggagaagc g                                            21

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 23
gggcatatgg cttctcctcc tgcttctg                                     28

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 24
gggggatcct taagtgccgc tctgaggact acg                               33

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 25
gggcccgggg cgcatcatgc acttctttga caaagcgac                         39

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 26
gggctgcagt taagtgccgc tctgaggact                                   30

```
<210> SEQ ID NO 27
<211> LENGTH: 13
<212> TYPE: PRT
<213> ORGANISM: Aspergillus sp. PF1224

<400> SEQUENCE: 27

Leu Tyr Asn Pro Asp Ser Pro Gln Pro Ile Ser Ala Lys
 1               5                  10

<210> SEQ ID NO 28
<211> LENGTH: 8
<212> TYPE: PRT
<213> ORGANISM: Aspergillus sp. PF1224

<400> SEQUENCE: 28

Leu Gln Phe Asn Pro Ala Pro Lys
 1               5

<210> SEQ ID NO 29
<211> LENGTH: 17
<212> TYPE: PRT
<213> ORGANISM: Aspergillus sp. PF1224

<400> SEQUENCE: 29

Val Asp Trp Phe Ser Asp Leu Thr Ser Thr Gly Gln Val Thr Gly Ser
 1               5                  10                  15

Lys

<210> SEQ ID NO 30
<211> LENGTH: 14
<212> TYPE: PRT
<213> ORGANISM: Aspergillus sp. PF1224

<400> SEQUENCE: 30

Gly Glu Val Ser Gly Ser Ala Ser Val Ser Ile Ile His Asp
 1               5                  10

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: y = c or t
<220> FEATURE:
<221> NAME/KEY: modified_base
<222> LOCATION: (6)
<223> OTHER INFORMATION: y = c or t
<220> FEATURE:
<221> NAME/KEY: modified_base
<222> LOCATION: (9)
<223> OTHER INFORMATION: n = a c g or t
<220> FEATURE:
<221> NAME/KEY: modified_base
<222> LOCATION: (12)
<223> OTHER INFORMATION: y = c or t
<220> FEATURE:
<221> NAME/KEY: modified_base
<222> LOCATION: (15)
<223> OTHER INFORMATION: n = a c g or t

<400> SEQUENCE: 31
tayaayccng aytcncc                                                17
```

```
<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: y = c or t
<220> FEATURE:
<221> NAME/KEY: modified_base
<222> LOCATION: (6)
<223> OTHER INFORMATION: y = c or t
<220> FEATURE:
<221> NAME/KEY: modified_base
<222> LOCATION: (9)
<223> OTHER INFORMATION: n = a c g or t
<220> FEATURE:
<221> NAME/KEY: modified_base
<222> LOCATION: (12)
<223> OTHER INFORMATION: y = c or t
<220> FEATURE:
<221> NAME/KEY: modified_base
<222> LOCATION: (15)
<223> OTHER INFORMATION: y = c or t

<400> SEQUENCE: 32
tayaayccng ayagycc                                                17

<210> SEQ ID NO 33
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: r = a or g
<220> FEATURE:
<221> NAME/KEY: modified_base
<222> LOCATION: (6)
<223> OTHER INFORMATION: y = c or t
<220> FEATURE:
<221> NAME/KEY: modified_base
<222> LOCATION: (9)
<223> OTHER INFORMATION: y = c or t
<220> FEATURE:
<221> NAME/KEY: modified_base
<222> LOCATION: (12)
<223> OTHER INFORMATION: n = a c g or t
<220> FEATURE:
<221> NAME/KEY: modified_base
<222> LOCATION: (15)
<223> OTHER INFORMATION: n = a c g or t

<400> SEQUENCE: 33
carttyaayc cngcncc                                                17

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: n = a c g or t
<220> FEATURE:
<221> NAME/KEY: modified_base
```

```
<222> LOCATION: (6)
<223> OTHER INFORMATION: n = a c g or t
<220> FEATURE:
<221> NAME/KEY: modified_base
<222> LOCATION: (9)
<223> OTHER INFORMATION: r = a or g
<220> FEATURE:
<221> NAME/KEY: modified_base
<222> LOCATION: (12)
<223> OTHER INFORMATION: r = a or g
<220> FEATURE:
<221> NAME/KEY: modified_base
<222> LOCATION: (15)
<223> OTHER INFORMATION: y = c or t

<400> SEQUENCE: 34
ggngcnggrt traaytg                                              17

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: r = a or g
<220> FEATURE:
<221> NAME/KEY: modified_base
<222> LOCATION: (6)
<223> OTHER INFORMATION: n = a c g or t
<220> FEATURE:
<221> NAME/KEY: modified_base
<222> LOCATION: (9)
<223> OTHER INFORMATION: r = a or g
<220> FEATURE:
<221> NAME/KEY: modified_base
<222> LOCATION: (15)
<223> OTHER INFORMATION: r = a or g

<400> SEQUENCE: 35
aartcngara accartc                                              17

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: r = a or g
<220> FEATURE:
<221> NAME/KEY: modified_base
<222> LOCATION: (6)
<223> OTHER INFORMATION: r = a or g
<220> FEATURE:
<221> NAME/KEY: modified_base
<222> LOCATION: (9)
<223> OTHER INFORMATION: r = a or g
<220> FEATURE:
<221> NAME/KEY: modified_base
<222> LOCATION: (15)
<223> OTHER INFORMATION: r = a or g

<400> SEQUENCE: 36
aartcrctra accartc                                              17

<210> SEQ ID NO 37
```

```
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 37
cctcgatacc cgagggaccg                                                  20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 38
gatgggttgc atgttatcgc                                                  20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 39
gcgataacat gcaacccatc                                                  20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: synthetic
      DNA

<400> SEQUENCE: 40
gaccacctgg ttcagtggtg                                                  20

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 41
gggttataga gtctggtaac g                                                21

<210> SEQ ID NO 42
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 42
gggaggcctg cgcatcatgc atgttgtcgc aagtaccac                             39

<210> SEQ ID NO 43
<211> LENGTH: 35
```

```
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 43
gggctcgagt acctcaagtc ccatttgccg gctgc                              35

<210> SEQ ID NO 44
<211> LENGTH: 12
<212> TYPE: PRT
<213> ORGANISM: Eupenicillium brefeldianum PF1226

<400> SEQUENCE: 44

Ser Thr Thr Pro Ala Pro Pro Gln Pro Glu Pro Ile
 1               5                  10

<210> SEQ ID NO 45
<211> LENGTH: 11
<212> TYPE: PRT
<213> ORGANISM: Eupenicillium brefeldianum PF1226

<400> SEQUENCE: 45

Ala Asp Pro Ala Phe Ser Pro Asp Gly Thr Arg
 1               5                  10

<210> SEQ ID NO 46
<211> LENGTH: 13
<212> TYPE: PRT
<213> ORGANISM: Eupenicillium brefeldianum PF1226

<400> SEQUENCE: 46

Leu His Pro Asp Asp Thr His Met Gly Trp Ser Ser Phe
 1               5                  10

<210> SEQ ID NO 47
<211> LENGTH: 16
<212> TYPE: PRT
<213> ORGANISM: Eupenicillium brefeldianum PF1226

<400> SEQUENCE: 47

Gly Phe Ser Gly Ala Gly Asp Glu Ile Leu Tyr Ile Gly Ser Thr Arg
 1               5                  10                  15

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: n = a c g or t
<220> FEATURE:
<221> NAME/KEY: modified_base
<222> LOCATION: (6)
<223> OTHER INFORMATION: r = a or g
<220> FEATURE:
<221> NAME/KEY: modified_base
<222> LOCATION: (9)
<223> OTHER INFORMATION: n = a c g or t
<220> FEATURE:
<221> NAME/KEY: modified_base
<222> LOCATION: (12)
<223> OTHER INFORMATION: r = a or g
<220> FEATURE:
```

```
<221> NAME/KEY: modified_base
<222> LOCATION: (15)
<223> OTHER INFORMATION: n = a c g or t

<400> SEQUENCE: 48
ccncarccng arccnat                                              17

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
<220> FEATURE:
<221> NAME/KEY: modified_base
<222> LOCATION: (3)
<223> OTHER INFORMATION: r = a or g
<220> FEATURE:
<221> NAME/KEY: modified_base
<222> LOCATION: (6)
<223> OTHER INFORMATION: n = a c g or t
<220> FEATURE:
<221> NAME/KEY: modified_base
<222> LOCATION: (9)
<223> OTHER INFORMATION: n = a c g or t
<220> FEATURE:
<221> NAME/KEY: modified_base
<222> LOCATION: (12)
<223> OTHER INFORMATION: r = a or g
<220> FEATURE:
<221> NAME/KEY: modified_base
<222> LOCATION: (15)
<223> OTHER INFORMATION: n = a c g or t

<400> SEQUENCE: 49
ctraangcng grtcngc                                              17

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: synthetic
      DNA
<220> FEATURE:
<221> NAME/KEY: modified_base
<222> LOCATION: (4)
<223> OTHER INFORMATION: n = a c g or t
<220> FEATURE:
<221> NAME/KEY: modified_base
<222> LOCATION: (10)
<223> OTHER INFORMATION: r = a or g
<220> FEATURE:
<221> NAME/KEY: modified_base
<222> LOCATION: (13)
<223> OTHER INFORMATION: n = a c g or t
<220> FEATURE:
<221> NAME/KEY: modified_base
<222> LOCATION: (16)
<223> OTHER INFORMATION: r = a or g

<400> SEQUENCE: 50
ccancccatr tgngtrtc                                             18

<210> SEQ ID NO 51
<211> LENGTH: 37
<212> TYPE: DNA
<213> ORGANISM: Artificial Sequence
<220> FEATURE:
<223> OTHER INFORMATION: Description of Artificial Sequence:synthetic
      DNA
```

```
<400> SEQUENCE: 51
gggcccgggc tcagactacc ccggcacctc ctcagcc                                37

<210> SEQ ID NO 52
<211> LENGTH: 38
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 52
gggctcgagt acctcatgca ccattgagcg gctggtgg                               38

<210> SEQ ID NO 53
<211> LENGTH: 1917
<212> TYPE: DNA
<213> ORGANISM: Neocosmospora vasinfecta variety vasinfecta P1225
<220> FEATURE:
<221> NAME/KEY: CDS
<222> LOCATION: (1)..(1914)
<220> FEATURE:
<221> NAME/KEY: mat_peptide
<222> LOCATION: (79)..(1914)

<400> SEQUENCE: 53 atg cac ttc ttt gac aaa gcg act gtc tac gct ata ctc tgc ggt agc         48
Met His Phe Phe Asp Lys Ala Thr Val Tyr Ala Ile Leu Cys Gly Ser
 -25                 -20                 -15 gtg gcc cag act gtt cac act gca ccc tcc gct tct cct cct gct tct         96
Val Ala Gln Thr Val His Thr Ala Pro Ser Ala Ser Pro Pro Ala Ser
-10                  -5                  -1   1                 5 gtt cca aac cct cct tct cct gag ccc att acc ctc aag cag cta cct        144
Val Pro Asn Pro Pro Ser Pro Glu Pro Ile Thr Leu Lys Gln Leu Pro
                 10                  15                  20 ctt cct ccc atc tcc cct agc gac gac gtc ggt gct tgc acg aag cag        192
Leu Pro Pro Ile Ser Pro Ser Asp Asp Val Gly Ala Cys Thr Lys Gln
             25                  30                  35 atc aac tct cgt gga acg gga tgt ctc gcc aac ggc gtt ttt gaa acg        240
Ile Asn Ser Arg Gly Thr Gly Cys Leu Ala Asn Gly Val Phe Glu Thr
         40                  45                  50 ttt cag tct ggt gac ttt tta cct gat gga aag cat gtc atc gcc atg        288
Phe Gln Ser Gly Asp Phe Leu Pro Asp Gly Lys His Val Ile Ala Met
 55                  60                  65                  70 gtc aac ttt act ggt gcg cct gct gct ccg gct gcg gga agc atc tac        336
Val Asn Phe Thr Gly Ala Pro Ala Ala Pro Ala Ala Gly Ser Ile Tyr
                 75                  80                  85 tct ggc ccg cag gtc atc atc gtc aag acg gat ggc aag aca ttt cct        384
Ser Gly Pro Gln Val Ile Ile Val Lys Thr Asp Gly Lys Thr Phe Pro
             90                  95                 100 aac gga gac ccc tgg aag tgc atc acc tgt ggt gtc cct gag aag aac        432
Asn Gly Asp Pro Trp Lys Cys Ile Thr Cys Gly Val Pro Glu Lys Asn
         105                 110                 115 gcc gtt ggt atc agc gtc aag tat gac tac ccc cag gcc ttt aag gat        480
Ala Val Gly Ile Ser Val Lys Tyr Asp Tyr Pro Gln Ala Phe Lys Asp
 120                 125                 130 ggc aaa cgt ctt ctc atc gga cac aat att ctc gac tgc ggt acc aac        528
Gly Lys Arg Leu Leu Ile Gly His Asn Ile Leu Asp Cys Gly Thr Asn
135                 140                 145                 150 cag ttg acg agc gag agc tgc aag cca gat aac acc cac atc tac cct        576
Gln Leu Thr Ser Glu Ser Cys Lys Pro Asp Asn Thr His Ile Tyr Pro
                 155                 160                 165
```

```
atc cgc tgg aat gtt gct gcc gac ggt tcc ggc ccg agc ggt gaa atc      624
Ile Arg Trp Asn Val Ala Ala Asp Gly Ser Gly Pro Ser Gly Glu Ile
        170                 175                 180 cgt gag ctg cgg tta cac ccg gac aat gtc cat ctc gag ttt agc tct      672
Arg Glu Leu Arg Leu His Pro Asp Asn Val His Leu Glu Phe Ser Ser
    185                 190                 195 ttc acc ttt gct agt ggc agt att gga cag tat gcc tac ttt tct cgg      720
Phe Thr Phe Ala Ser Gly Ser Ile Gly Gln Tyr Ala Tyr Phe Ser Arg
    200                 205                 210 ctc gtt ttc aat cct tcg ccc aag act gga act ccc ctt gcg ccg cgg      768
Leu Val Phe Asn Pro Ser Pro Lys Thr Gly Thr Pro Leu Ala Pro Arg
215                 220                 225                 230 tat gac ctg gaa aag gtt act att ctg cac aac ccc gag ggc gtt gcc      816
Tyr Asp Leu Glu Lys Val Thr Ile Leu His Asn Pro Glu Gly Val Ala
                235                 240                 245 cct atc acg gcc aag ggt aag gtt ctg tct ctg aac ccc cag gct att      864
Pro Ile Thr Ala Lys Gly Lys Val Leu Ser Leu Asn Pro Gln Ala Ile
            250                 255                 260 tcg gtt ggc gag gct cgt ggc ttc aac ggc gac gga act gag ctc act      912
Ser Val Gly Glu Ala Arg Gly Phe Asn Gly Asp Gly Thr Glu Leu Thr
        265                 270                 275 tat gtc gga agc aat att gag agc tgt aat aat gat gtc ttt gcc gtt      960
Tyr Val Gly Ser Asn Ile Glu Ser Cys Asn Asn Asp Val Phe Ala Val
    280                 285                 290 cat ctt caa act gga gtt gtt cga cgt ctt acc aac cat ccc gag tat     1008
His Leu Gln Thr Gly Val Val Arg Arg Leu Thr Asn His Pro Glu Tyr
295                 300                 305                 310 cct gac cct ctg gct ttc tcg cct gat aac aaa tgg atg gct gtc atg     1056
Pro Asp Pro Leu Ala Phe Ser Pro Asp Asn Lys Trp Met Ala Val Met
                315                 320                 325 gat acc cgc gga agt ggt cgc aac atg ttt att gcc ggc atg cga gga     1104
Asp Thr Arg Gly Ser Gly Arg Asn Met Phe Ile Ala Gly Met Arg Gly
            330                 335                 340 atc ccg ccc ctg gtt gat att gtt ggc ggt att ctg cca gcg tcg tct     1152
Ile Pro Pro Leu Val Asp Ile Val Gly Gly Ile Leu Pro Ala Ser Ser
        345                 350                 355 cgc aac aac ggt ctt cgt cgc ttc ttc cag ccg tac ctg ctt gat ttt     1200
Arg Asn Asn Gly Leu Arg Arg Phe Phe Gln Pro Tyr Leu Leu Asp Phe
    360                 365                 370 tat ggt gac cgc ggt gac tac tac ggc caa aag ttc aac gga gat aac     1248
Tyr Gly Asp Arg Gly Asp Tyr Tyr Gly Gln Lys Phe Asn Gly Asp Asn
375                 380                 385                 390 aat ggc gtg cct ggg agt ggt gcc atc aac gat cct gag tgg aac ggt     1296
Asn Gly Val Pro Gly Ser Gly Ala Ile Asn Asp Pro Glu Trp Asn Gly
                395                 400                 405 atg gct gat ccg aga tgg tct cct gac cgc agg cag ctc gtc ttt tgg     1344
Met Ala Asp Pro Arg Trp Ser Pro Asp Arg Arg Gln Leu Val Phe Trp
            410                 415                 420 cag act cat acc gtc tcc cct tct tgt ggc ggc gcc aac cct ctc cct     1392
Gln Thr His Thr Val Ser Pro Ser Cys Gly Gly Ala Asn Pro Leu Pro
        425                 430                 435 tgc tac cct tcg aaa gag caa ggt ggc cgt aac tat cgc atg tac atc     1440
Cys Tyr Pro Ser Lys Glu Gln Gly Gly Arg Asn Tyr Arg Met Tyr Ile
    440                 445                 450 gcg acc ttt act agc cgc agc cca agc cct cct gcc ccg gtg aag gag     1488
Ala Thr Phe Thr Ser Arg Ser Pro Ser Pro Pro Ala Pro Val Lys Glu
455                 460                 465                 470 cac tcc gat acc atc ccc tgg ggc gtc ccg tac gtt ccc gga tct cag     1536
His Ser Asp Thr Ile Pro Trp Gly Val Pro Tyr Val Pro Gly Ser Gln
                475                 480                 485
```

```
gtt act cca aag cct ggc ttg gcg ggc ggt atc tac acg ctc tac ggc      1584
Val Thr Pro Lys Pro Gly Leu Ala Gly Gly Ile Tyr Thr Leu Tyr Gly
        490                 495                 500 aag gct tcg ggc gag gcc aag gtc aac atc acc tgg ggt gag gca ccc      1632
Lys Ala Ser Gly Glu Ala Lys Val Asn Ile Thr Trp Gly Glu Ala Pro
        505                 510                 515 gag att gga acc gtc agc gtc gtg tac aag gac tat tcg ctc gac ggc      1680
Glu Ile Gly Thr Val Ser Val Val Tyr Lys Asp Tyr Ser Leu Asp Gly
    520                 525                 530 aag agc ttc ctc aac ggg aac gag agc gtc acg ggg tct gtc gag aga      1728
Lys Ser Phe Leu Asn Gly Asn Glu Ser Val Thr Gly Ser Val Glu Arg
535                 540                 545                 550 ctg act gac tat tct ttt gac tgg tat tcg gat att cgc cag acg gga      1776
Leu Thr Asp Tyr Ser Phe Asp Trp Tyr Ser Asp Ile Arg Gln Thr Gly
                555                 560                 565 gct gtc aag gga acc aag aag acg agc cct ggt gga ttc cat gct aat      1824
Ala Val Lys Gly Thr Lys Lys Thr Ser Pro Gly Gly Phe His Ala Asn
            570                 575                 580 att gat gtc atg atc aac gac ctg act tca act ggt act ctt acc acg      1872
Ile Asp Val Met Ile Asn Asp Leu Thr Ser Thr Gly Thr Leu Thr Thr
                585                 590                 595 act ctg gat ggt gtt gag tgg cgt agt cct cag agc ggc act taa          1917
Thr Leu Asp Gly Val Glu Trp Arg Ser Pro Gln Ser Gly Thr
600                 605                 610

<210> SEQ ID NO 54
<211> LENGTH: 638
<212> TYPE: PRT
<213> ORGANISM: Neocosmospora vasinfecta variety vasinfecta P1225

<400> SEQUENCE: 54

Met His Phe Phe Asp Lys Ala Thr Val Tyr Ala Ile Leu Cys Gly Ser
        -25                 -20                 -15

Val Ala Gln Thr Val His Thr Ala Pro Ser Ala Ser Pro Pro Ala

```
Arg Glu Leu Arg Leu His Pro Asp Asn Val His Leu Glu Phe Ser Ser
            185                 190                 195

Phe Thr Phe Ala Ser Gly Ser Ile Gly Gln Tyr Ala Tyr Phe Ser Arg
            200                 205                 210

Leu Val Phe Asn Pro Ser Pro Lys Thr Gly Thr Pro Leu Ala Pro Arg
215                 220                 225                 230

Tyr Asp Leu Glu Lys Val Thr Ile Leu His Asn Pro Glu Gly Val Ala
            235                 240                 245

Pro Ile Thr Ala Lys Gly Lys Val Leu Ser Leu Asn Pro Gln Ala Ile
            250                 255                 260

Ser Val Gly Glu Ala Arg Gly Phe Asn Gly Asp Gly Thr Glu Leu Thr
            265                 270                 275

Tyr Val Gly Ser Asn Ile Glu Ser Cys Asn Asn Asp Val Phe Ala Val
            280                 285                 290

His Leu Gln Thr Gly Val Val Arg Arg Leu Thr Asn His Pro Glu Tyr
295                 300                 305                 310

Pro Asp Pro Leu Ala Phe Ser Pro Asp Asn Lys Trp Met Ala Val Met
            315                 320                 325

Asp Thr Arg Gly Ser Gly Arg Asn Met Phe Ile Ala Gly Met Arg Gly
            330                 335                 340

Ile Pro Pro Leu Val Asp Ile Val Gly Gly Ile Leu Pro Ala Ser Ser
            345                 350                 355

Arg Asn Asn Gly Leu Arg Arg Phe Phe Gln Pro Tyr Leu Leu Asp Phe
            360                 365                 370

Tyr Gly Asp Arg Gly Asp Tyr Tyr Gly Gln Lys Phe Asn Gly Asp Asn
375                 380                 385                 390

Asn Gly Val Pro Gly Ser Gly Ala Ile Asn Asp Pro Glu Trp Asn Gly
            395                 400                 405

Met Ala Asp Pro Arg Trp Ser Pro Asp Arg Arg Gln Leu Val Phe Trp
            410                 415                 420

Gln Thr His Thr Val Ser Pro Ser Cys Gly Gly Ala Asn Pro Leu Pro
            425                 430                 435

Cys Tyr Pro Ser Lys Glu Gln Gly Gly Arg Asn Tyr Arg Met Tyr Ile
            440                 445                 450

Ala Thr Phe Thr Ser Arg Ser Pro Ser Pro Ala Pro Val Lys Glu
455                 460                 465                 470

His Ser Asp Thr Ile Pro Trp Gly Val Pro Tyr Val Pro Gly Ser Gln
            475                 480                 485

Val Thr Pro Lys Pro Gly Leu Ala Gly Gly Ile Tyr Thr Leu Tyr Gly
            490                 495                 500

Lys Ala Ser Gly Glu Ala Lys Val Asn Ile Thr Trp Gly Glu Ala Pro
            505                 510                 515

Glu Ile Gly Thr Val Ser Val Val Tyr Lys Asp Tyr Ser Leu Asp Gly
            520                 525                 530

Lys Ser Phe Leu Asn Gly Asn Glu Ser Val Thr Gly Ser Val Glu Arg
535                 540                 545                 550

Leu Thr Asp Tyr Ser Phe Asp Trp Tyr Ser Asp Ile Arg Gln Thr Gly
            555                 560                 565

Ala Val Lys Gly Thr Lys Lys Thr Ser Pro Gly Gly Phe His Ala Asn
            570                 575                 580
```

```
Ile Asp Val Met Ile Asn Asp Leu Thr Ser Thr Gly Thr Leu Thr Thr
        585                 590                 595

Thr Leu Asp Gly Val Glu Trp Arg Ser Pro Gln Ser Gly Thr
    600                 605                 610
```